US012595408B2

(12) United States Patent
Miyazaki et al.

(10) Patent No.: US 12,595,408 B2
(45) Date of Patent: Apr. 7, 2026

(54) PHOTOCHROMIC COMPOUND, NAPHTHOL DERIVATIVE, CURABLE COMPOSITION, OPTICAL ARTICLE, LENS, AND EYEGLASSES

(71) Applicant: TOKUYAMA CORPORATION, Yamaguchi (JP)

(72) Inventors: Masayuki Miyazaki, Yamaguchi (JP); Srinivas Venu, Yamaguchi (JP); Katsuhiro Mori, Yamaguchi (JP)

(73) Assignee: TOKUYAMA CORPORATION, Yamaguchi (JP)

( * ) Notice: Subject to any disclaimer, the term of this patent is extended or adjusted under 35 U.S.C. 154(b) by 111 days.

(21) Appl. No.: 18/730,613

(22) PCT Filed: Jan. 13, 2023

(86) PCT No.: PCT/JP2023/000751

§ 371 (c)(1),
(2) Date: Jul. 19, 2024

(87) PCT Pub. No.: WO2023/140186

PCT Pub. Date: Jul. 27, 2023

(65) Prior Publication Data

US 2025/0101294 A1 Mar. 27, 2025

(30) Foreign Application Priority Data

Jan. 24, 2022 (JP) ................................ 2022-008896

(51) Int. Cl.

| | |
|---|---|
| ***C09K 9/02*** | (2006.01) |
| ***C07C 39/42*** | (2006.01) |
| ***C07C 43/23*** | (2006.01) |
| ***C07C 217/78*** | (2006.01) |
| ***C07C 323/21*** | (2006.01) |
| ***C07D 311/94*** | (2006.01) |
| ***C07D 317/70*** | (2006.01) |
| ***C07D 327/04*** | (2006.01) |
| ***C07D 493/04*** | (2006.01) |
| ***C07D 497/04*** | (2006.01) |
| ***C08K 5/1545*** | (2006.01) |
| ***C08K 5/1565*** | (2006.01) |
| ***C08K 5/357*** | (2006.01) |
| ***C09B 57/02*** | (2006.01) |
| ***G02B 1/04*** | (2006.01) |
| ***G02C 7/10*** | (2006.01) |

(52) U.S. Cl.

CPC ................ *C09K 9/02* (2013.01); *C07C 39/42* (2013.01); *C07C 43/23* (2013.01); *C07C 217/78* (2013.01); *C07C 323/21* (2013.01); *C07D 311/94* (2013.01); *C07D 317/70* (2013.01); *C07D 327/04* (2013.01); *C07D 493/04* (2013.01); *C07D 497/04* (2013.01); *C08K 5/1545* (2013.01); *C08K 5/1565* (2013.01); *C08K 5/357* (2013.01); *C09B 57/02* (2013.01); *G02B 1/041* (2013.01); *C07C 2603/40* (2017.05); *C09K 2211/1018* (2013.01); *G02C 7/102* (2013.01)

(58) Field of Classification Search

CPC ... C09K 9/02; C09K 2211/1018; C07C 39/42; C07C 43/23; C07C 217/78; C07C 323/21; C07C 2603/40; C07D 311/94; C07D 317/70; C07D 327/04; C07D 493/04; C08K 5/357; C08K 5/1545; C08K 5/1565; C09B 57/02; G02B 1/041; G02C 7/102

See application file for complete search history.

(56) References Cited

U.S. PATENT DOCUMENTS

| | | | | |
|---|---|---|---|---|
| 2003/0096117 A1 | 5/2003 | Kawabata et al. | | |
| 2004/0191520 A1* | 9/2004 | Kumar ..................... | C09K 9/02 428/411.1 | |
| 2007/0278461 A1* | 12/2007 | Petrovskaia .......... | C07F 7/1804 544/149 | |

(Continued)

FOREIGN PATENT DOCUMENTS

| | | |
|---|---|---|
| JP | 2007-524857 A | 8/2007 |
| JP | 2008-507618 A | 3/2008 |

(Continued)

OTHER PUBLICATIONS

International Search Report issued WIPO Patent Application No. PCT/JP2023/000163, dated Mar. 20, 2023, along with an English translation thereof.

Clive et al., "Formal Radical Cyclization onto Benzene Rings: A General Method and Its Use in the Synthesis of ent-Nocardione A", Journal of Organic Chemistry 69 (10) , Apr. 17, 2004, pp. 3282-3293.

(Continued)

*Primary Examiner* — Bijan Ahvazi

(74) *Attorney, Agent, or Firm* — GREENBLUM & BERNSTEIN, P.L.C.

(57) ABSTRACT

The purpose of the present invention is to provide: a photochromic compound having an excellent color fading rate and excellent durability; a naphthol derivative that can become an intermediate for the photochromic compound; and a curable composition, an optical article, a lens and eyeglasses each containing the photochromic compound. According to embodiments, a photochromic compound having a backbone represented by formula (1) is provided. In formula (1), M represents C, Si or Ge; $R^1$ represents a haloalkyl group having 1 to 20 carbon atoms inclusive; $R^2$ represents a substituted or unsubstituted alkyl group having 1 to 20 carbon atoms inclusive or a substituted or unsubstituted haloalkyl group having 1 to 20 carbon atoms inclusive.

13 Claims, No Drawings

(56) References Cited

U.S. PATENT DOCUMENTS

| | | | | |
|---|---|---|---|---|
| 2011/0143141 | A1* | 6/2011 | He | G03C 1/73 544/150 |
| 2014/0034884 | A1* | 2/2014 | Takahashi | C09K 9/02 544/70 |
| 2014/0054520 | A1 | 2/2014 | Takenaka et al. | |
| 2020/0172681 | A1 | 6/2020 | Takenaka et al. | |
| 2021/0032532 | A1 | 2/2021 | Miyazaki et al. | |

FOREIGN PATENT DOCUMENTS

| | | | |
|---|---|---|---|
| JP | 2008-535971 | A | 9/2008 |
| JP | 2009-538974 | A | 11/2009 |
| JP | 2019-182866 | A | 10/2019 |
| WO | 96/14596 | A1 | 5/1996 |
| WO | 00/15630 | A1 | 3/2000 |
| WO | 01/60811 | A1 | 8/2001 |
| WO | 2004/085568 | A2 | 10/2004 |
| WO | 2004/086103 | A1 | 10/2004 |
| WO | 2006/022825 | A1 | 3/2006 |
| WO | 2006/110219 | A1 | 10/2006 |
| WO | 2006/110221 | A1 | 10/2006 |
| WO | 2007/140071 | A1 | 12/2007 |
| WO | 2011/053615 | A1 | 5/2011 |
| WO | 2012/102410 | A1 | 8/2012 |
| WO | 2012/121414 | A1 | 9/2012 |
| WO | 2013/086248 | A1 | 6/2013 |
| WO | 2015/035325 | A1 | 3/2015 |
| WO | 2018/235771 | A1 | 12/2018 |

OTHER PUBLICATIONS

Gourdoupis et al., "A Direct and Versatile Synthesis of 5-(2-Di-n-Propylaminoethyl)-7-methoxyindole", Synthetic Communications 23(16), 1993, pp. 2241-2249.

Ureshino et al., "Rhodium-Catalyzed Synthesis of Silafluorene Derivatives via Cleavage of Silicon-Hydrogen and Carbon-Hydrogen Bonds", J. Am. Chem. Soc. 132(41), Sep. 24, 2010, pp. 14324-14326.

Murai et al., "Rhodium-Catalyzed Dehydrogenative Germylation of C—H Bonds: New Entry to Unsymmetrically Functionalized 9-Germafluorenes", Org, Lett. 16, Dec. 10, 2014, pp. 6492-6495.

International Search Report iissued in International Bureau of WIPO Patent Application No. PCT/JP2023/000751, dated Apr. 4, 2023, along with an English translation thereof.

U.S. Appl. No. 18/729,281 to Masayuki Miyazaki et al., filed Jul. 16, 2024.

Extended European Search Report that issued in European Patent Application No. 23743180.4, dated Feb. 18, 2025.

* cited by examiner

PHOTOCHROMIC COMPOUND, NAPHTHOL DERIVATIVE, CURABLE COMPOSITION, OPTICAL ARTICLE, LENS, AND EYEGLASSES

TECHNICAL FIELD

The present invention relates to a photochromic compound, a naphthol derivative, a curable composition, an optical article, a lens, and eyeglasses.

BACKGROUND ART

Photochromic compounds are compounds that can reversibly take two isomeric forms with different absorption spectra upon irradiation with light including ultraviolet light such as sunlight or light from a mercury vapor lamp. In general, a compound in a colorless or decolored state quickly changes in color and is isomerized (chromogenic reaction) to a colored or color-developed state by irradiation with ultraviolet light. The photochromic compounds have been studied and developed as materials for photochromic lenses.

In applications of such photochromic lenses, the photochromic compounds may require the following properties:

(I) a degree of coloration in a visible light range before irradiation with ultraviolet light (hereinafter referred to as initial coloration) is low;

(II) a color developing density (hereinafter referred to as color developing density) quickly reaches a saturation level from the beginning of irradiation with ultraviolet light;

(III) a color developing density quickly reaches a saturation level from the beginning of irradiation with ultraviolet light (hereinafter also referred to as high color developing sensitivity);

(IV) a color quickly returns to its original state after irradiation with ultraviolet light is stopped (hereinafter referred to as color fading rate);

(V) repetition durability of the above-mentioned reversible action is high; and (VI) solubility in a material that makes up a matrix of a lens is high and dispersibility within a cured product is high.

A number of chromene compounds have been studied as photochromic compounds that satisfy these properties. For example, a chromene compound represented by Formula (A) below (Patent Document 1), a chromene compound represented by Formula (B) below (Patent Document 2), and a chromene compound represented by Formula (C) below (Patent Document 3) have been known.

[Chem. 1]

(A)

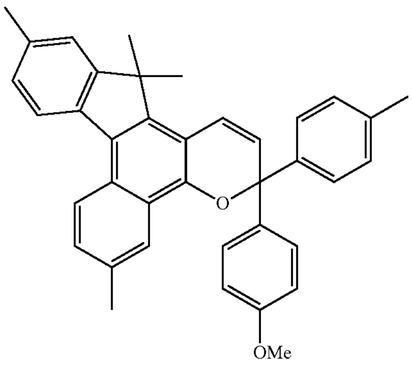

-continued

[Chem. 2]

(B)

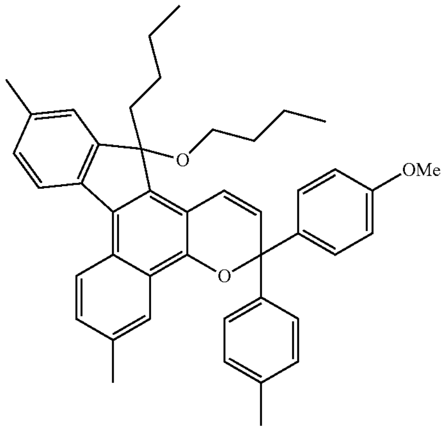

[Chem. 3]

(C)

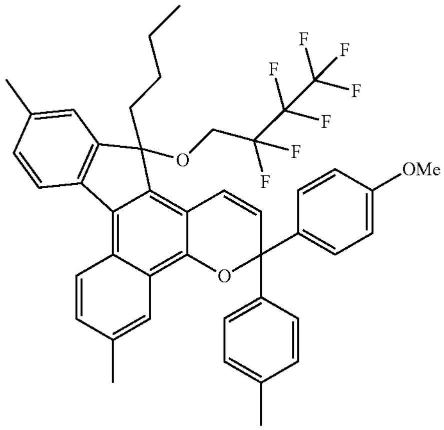

CITATION LIST

Patent Document

Patent Document 1: PCT International Publication No. WO1996/014596

Patent Document 2: PCT International Publication No. WO2004/085568

Patent Document 3: PCT International Publication No. WO2007/1400711

Patent Document 4: PCT International Publication No. WO2001/060811

Patent Document 5: PCT International Publication No. WO2015/035325

Patent Document 6: PCT International Publication No. WO2012/121414

Patent Document 7: PCT International Publication No. WO2006/110221

Patent Document 8: PCT International Publication No. WO2011/053615

Patent Document 9: PCT International Publication No. WO2006/110219

Non-Patent Document

Non-Patent Document 1: Journal of Organic Chemistry 69 (10) 3282-3293; 2004

Non-Patent Document 2: Synthetic Communications 23 (16) 2241-2249 (1993)
Non-Patent Document 3: J. Am. Chem. Soc. 132 (41) 14324-14326 (2010)
Non-Patent Document 4: Org. Lett. 16, 6492-6495 (2014)

DISCLOSURE OF THE INVENTION

Problems to be Solved by the Invention

An object of the present invention is to provide a photochromic compound with an excellent color fading rate and durability; a naphthol derivative that can be an intermediate of the photochromic compound; and a curable composition, an optical article, a lens, and eyeglasses including the photochromic compound.

Means for Solving the Problems

According to an embodiment, there is provided a photochromic compound having a backbone represented by Formula (1) below:

[Chem. 4]

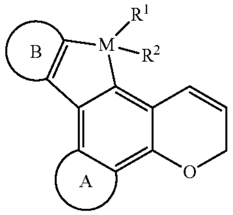

(1)

In Formula (1), M is C, Si, or Ge. $R^1$ is a haloalkyl group having 1 or more and 20 or less carbon atoms. $R^2$ is a substituted or unsubstituted alkyl group having 1 or more and 20 or less carbon atoms or a substituted or unsubstituted haloalkyl group having 1 or more and 20 or less carbon atoms.

Ring A is a substituted or unsubstituted aromatic hydrocarbon ring, a substituted or unsubstituted aromatic heterocyclic ring, or a substituted or unsubstituted fused polycyclic ring in which an aromatic ring or an aromatic heterocyclic ring is fused to any of the above-mentioned rings. Ring A may not be present. Ring B is a substituted or unsubstituted aromatic hydrocarbon ring, a substituted or unsubstituted aromatic heterocyclic ring, or a substituted or unsubstituted fused polycyclic ring in which an aromatic ring or an aromatic heterocyclic ring is fused to any of the above-mentioned rings.

According to another embodiment, a curable composition is provided. The curable composition includes a photochromic compound according to the embodiment; and at least one selected from the group consisting of a radical polymerizable monomer, a cationic polymerizable monomer, a compound having a polymerization reactive group, and a (thio)urethane(urea) polymer.

According to another embodiment, an optical article is provided. The optical article includes a cured product of the curable composition.

According to another embodiment, a lens is provided. The lens includes a photochromic compound according to the embodiment.

According to another embodiment, eyeglasses are provided. The eyeglasses include the lens according to the embodiment.

According to another embodiment, a naphthol derivative is provided. The naphthol derivative has a backbone represented by Formula (5) below:

[Chem. 5]

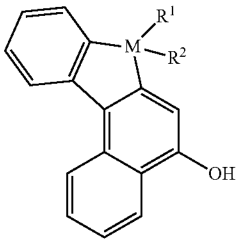

(5)

In Formula (5), M, $R^1$, and $R^2$ are each independently the same as in Formula (1) above.

Effects of the Invention

According to the present invention, there is provided a photochromic compound that has an excellent color fading rate and durability; a naphthol derivative that can be an intermediate of the photochromic compound; and a curable composition, an optical article, a lens, and eyeglasses including the photochromic compound.

PREFERRED MODE FOR CARRYING OUT THE INVENTION

[Photochromic Compound]

According to an embodiment, there is provided a photochromic compound having a backbone represented by Formula (1) below:

[Chem. 6]

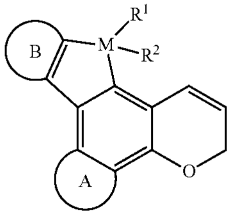

(1)

In Formula (1), M is C, Si, or Ge. $R^1$ is a haloalkyl group having 1 or more and 20 or less carbon atoms. $R^2$ is a substituted or unsubstituted alkyl group having 1 or more and 20 or less carbon atoms or a substituted or unsubstituted haloalkyl group having 1 or more and 20 or less carbon atoms. Ring A is a substituted or unsubstituted aromatic hydrocarbon ring, a substituted or unsubstituted aromatic heterocyclic ring, or a substituted or unsubstituted fused polycyclic ring in which an aromatic ring or an aromatic heterocyclic ring is fused to any of the above-mentioned rings. Ring A may not be present. Ring B is a substituted or unsubstituted aromatic hydrocarbon ring, a substituted or unsubstituted aromatic heterocyclic ring, or a substituted or unsubstituted fused polycyclic ring in which an aromatic ring or an aromatic heterocyclic ring is fused to any of the above-mentioned rings.

This photochromic compound has an excellent color fading rate and durability. The reasons for this are believed to be as follows. First, the inventors have found that a substituent attached to an atom at position 13 in a photochromic compound having a backbone represented by Formula (1) has a significant effect on the color fading rate. As a result of extensive studies, the present inventors have found that a photochromic compound in which $R^1$ and $R^2$ are each an alkyl group is less likely to cause a steric hindrance and structural change to a colorless isomer. It is believed that this is because alkyl groups aggregate with each other by the action of a van der Waals force between the alkyl groups. Thus, the photochromic compounds in which $R^1$ and $R^2$ are each an alkyl group have been found to have a lower color fading rate. In a photochromic compound according to the embodiment, $R^1$ is a haloalkyl group having 1 or more and 20 or less carbon atoms. $R^2$ is a substituted or unsubstituted alkyl group having 1 or more and 20 or less carbon atoms or a substituted or unsubstituted haloalkyl group having 1 or more and 20 or less carbon atoms. In other words, in the photochromic compound according to the embodiment, $R^1$ and $R^2$ are each a haloalkyl group or a combination of a haloalkyl group and an alkyl group.

When $R^1$ and $R^2$ have such a structure, a van der Waals force is decreased, which is thought to increase a color fading rate of the photochromic compound. Thus, the photochromic compound according to the embodiment can exhibit a high color fading rate. Furthermore, as a result of extensive studies, the present inventors have also found that durability of a photochromic compound is increased by introducing substituents $R^1$ and $R^2$ into an atom M at position 13 without an intervening oxygen atom (O). In other words, in a photochromic compound according to the embodiment, a haloalkyl group or an alkyl group is directly attached to an atom M at position 13, and no oxygen atom is attached thereto. Therefore, the photochromic compound according to the embodiment is more durable compared to a photochromic compound having a substituent introduced via an oxygen atom such as an alkoxy group or a haloalkyl group.

In light of the above, the photochromic compound according to the embodiments can be used to achieve a cured product with an excellent color fading rate and durability. Therefore, such a photochromic compound is suitable for an optical article to be used in an environment with a large temperature variation such as sunglasses.

A photochromic compound having a backbone represented by Formula (1) will be described in detail.

<M>

In Formula (1), M is C, Si, or Ge. M is preferably C or Si.

<$R^1$>

$R^1$ is a substituted or unsubstituted haloalkyl group having 1 or more and 20 or less carbon atoms. The haloalkyl group has preferably 1 or more and 20 or less carbon atoms, more preferably 1 or more and 12 or less carbon atoms, further preferably 1 or more and 7 or less carbon atoms, and most preferably 2 or more and 6 or less carbon atoms. At least one halogen atom selected from the group consisting of I, Cl, Br, and F may be used. The halogen atom is preferably at least one of C1 or F and more preferably F.

The haloalkyl group preferably have one or more halogen atoms, preferably three halogen atoms attached to a terminal carbon atom. A haloalkyl group having a halogen atom attached to a terminal carbon atom tends to easily cause steric hindrance.

The haloalkyl group is, for example, represented by Formula (A) below:

$$—C_\alpha H_\beta Z_\gamma \quad (A)$$

In formula (A), α is a number of carbon atoms. α is preferably 1 or more and 10 or less and more preferably 2 or more and 6 or less.

β is a number of hydrogen atoms.

β is, for example, 1 or more and 20 or less, preferably 2 or more and 12 or less, and more preferably 4 or more and 10 or less. However, $\beta+\gamma=2\alpha+1$.

Z denotes a halogen atom.

γ is a number of halogen atoms.

γ is, for example, 1 or more and 20 or less, preferably 2 or more and 12 or less, and more preferably 3 or more and 6 or less.

$R^1$ may be a group represented by Formula (1a) below;

$$—(CH_\delta X^{11}_\varepsilon)_\theta—CH_\zeta X^{12}_\eta \quad (1a)$$

In Formula (1a), $X^{11}$ and $X^{12}$ are each independently a halogen atom. The halogen atom is preferably fluorine (F).

δ and ε are independently 0 or 1 or 2.

$\delta+\varepsilon=2$. It is preferred that δ be 2 and ε be 0. In other words, $—CH_\delta X^{11}_\varepsilon—$ is preferably a methylene group ($—CH_2—$).

θ is a number of repeats of $—CH_\delta X^{11}_\varepsilon—$.

θ is 0, or 1 or more and 10 or less.

θ is preferably 1 or more and 8 or less, more preferably 2 or more and 6 or less, and further preferably 3 or more and 5 or less. A smaller number of θ tends to increase a color fading rate. A larger number of θ tends to increase a color developing density.

ζ is 0 or 1 or 2.

η is 1 or more and 3 or less.

$\zeta+\eta=3$. It may be that ζ is 2 and η is 1, that is, $CH_\zeta X^{12}_\eta$ may be a monohaloalkyl group. When $CH_\zeta X^{12}_\eta$ is a monohaloalkyl group, a color developing density tends to increase. It may be that ζ is 0 and η is 3, that is, $CH_\zeta X^{12}_\eta$ may be a perhaloalkyl group. When $CH_\zeta X^{12}_\eta$ is a perhaloalkyl group, a color fading rate tends to increase.

<$R^2$>

$R^2$ is a substituted or unsubstituted alkyl group having 1 or more and 20 or less carbon atoms or a substituted or unsubstituted haloalkyl group having 1 or more and 20 or less carbon atoms. $R^2$ is preferably a substituted or unsubstituted haloalkyl group having 1 or more and 20 or less carbon atoms. When $R^2$ is a haloalkyl group, steric hindrance tends to easily occur and a color fading rate tends to increase. When $R^2$ is a haloalkyl group, it may have a structure that is the same as or different from that for $R^1$, but the same structure is preferred from the viewpoint of synthesis. A preferred form of the haloalkyl group is the same as for $R^1$. $R^2$ is preferably a group represented by Formula (1a).

The alkyl group has preferably 1 or more and 20 or less carbon atoms, more preferably 1 or more and 12 or less carbon atoms, and most preferably 2 or more and 7 or less carbon atoms.

<Ring A>

In Formula (1), Ring A is a substituted or unsubstituted aromatic hydrocarbon ring, a substituted or unsubstituted aromatic heterocyclic ring, or a substituted or unsubstituted fused polycyclic ring in which an aromatic ring or an aromatic heterocyclic ring is fused to any of the above-mentioned rings. Furthermore, Ring A is not essential and may not be present.

Examples of the aromatic hydrocarbon ring include a benzene ring or a cyclotetradecaheptaene ring.

Examples of the aromatic heterocyclic ring include a furan ring, a thiophene ring, or a pyridine ring.

Examples of the fused polycyclic ring include a naphthalene ring, a fluorene ring, an anthracene ring, a phenanthrene ring, a tetracene ring, a pentacene ring, a benzopyrene ring, a chrysene ring, a pyrene ring, a triphenylene ring, a perylene ring, a benzofuran ring, a benzothiophene ring, a quinoline ring, an isoquinoline ring, an indole ring, a pyrimidine ring, a quinazoline ring, a pyridazine ring, a cinnoline ring, a phthalazine ring, a 1,2,3-, 1,2,4-, or 1,3,5-triazine ring, a carbazole ring, a benzoxazole ring, or an isothiazole ring.

Among them, a benzene ring, a naphthalene ring, a fluorene ring, a phenanthrene ring, a pyrene ring, a furan ring, a thiophene ring, or a pyridine ring is preferred and a benzene ring, a naphthalene ring, a fluorene ring, or a phenanthrene ring is most preferred.

<Ring B>

In Formula (1), Ring B is a substituted or unsubstituted aromatic hydrocarbon ring, a substituted or unsubstituted aromatic heterocyclic ring, or a substituted or unsubstituted fused polycyclic ring in which an aromatic ring or an aromatic heterocyclic ring is fused to any of the above-mentioned rings. With regard to a suitable ring B, the same applies as for Ring A.

<Compound represented by Formula (2)>

A photochromic compound according to the embodiment preferably has a naphthopyran backbone represented by Formula (2) below. In Formula (2) below, $R^1$, $R^2$, and M are each the same as in Formula (1).

[Chem. 7]

(2)

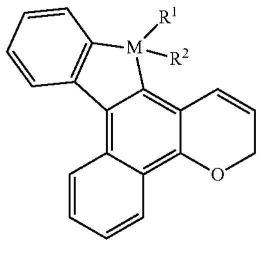

<Compound represented by Formula (3)>

A photochromic compound according to the embodiment is preferably a compound represented by Formula (3) below. In Formula (4) below, $R^1$, $R^2$, and M are each the same as in Formula (1).

[Chem. 8]

(3)

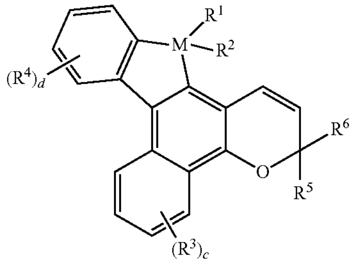

<$R^3$ and $R^4$>

$R^3$ and $R^4$ are each independently a hydroxyl group, an optionally substituted alkyl group, an optionally substituted haloalkyl group, an optionally substituted cycloalkyl group, an alkoxy group, an amino group, a substituted amino group, an optionally substituted heterocyclic group, a cyano group, a halogen atom, an alkylthio group, an optionally substituted arylthio group, a nitro group, a formyl group, a hydroxycarbonyl group, an alkylcarbonyl group, an alkoxycarbonyl group, an optionally substituted aralkyl group, an optionally substituted aralkoxy group, an optionally substituted aryloxy group, an optionally substituted aryl group, an optionally substituted heteroaryl group, a thiol group, an alkoxyalkylthio group, a haloalkylthio group, or an optionally substituted cycloalkylthio group, an optionally substituted silyl group, an optionally substituted oxysilyl group, a group represented by Formula (X) below, a group represented by $L^1$-$R^{400}$ below, or a group represented by Formula (Y) below.

c is an integer of 0 to 4.

d is an integer of 0 to 4.

When c is 2 to 4, a plurality of $R^3$s may be the same as or different from each other. When c is 2 to 4 and adjacent $R^3$s are present, two adjacent $R^3$s may be taken together with a carbon atom to which $R^3$s are attached to form a ring optionally including an oxygen atom, a carbon atom, a sulfur atom, or a nitrogen atom and the ring is optionally substituted. Examples of a combination of the adjacent $R^3$s include $R^3$s at positions 5 and 6, positions 6 and 7, or positions 7 and 8 of the chromene compound.

When d is 2 to 4, a plurality of $R^4$s may be the same as or different from each other. When d is 2 to 4 and adjacent $R^4$s are present, two adjacent $R^4$s may be taken together with a carbon atom to which $R^4$s are attached to form a ring optionally including an oxygen atom, a carbon atom, a sulfur atom, or a nitrogen atom and the ring is optionally substituted. Examples of a combination of the adjacent $R^4$s include $R^4$s at positions 9 and 10, positions 10 and 11, or positions 11 and 12 of the chromene compound.

A ring having 5 to 8 atoms including a carbon atom to which $R^3$ and $R^4$ are attached is preferably formed. The ring may have a substituent and the substituent may be a substituent selected from a hydroxyl group, an alkyl group having 1 to 6 carbon atoms, a haloalkyl group having 1 to 6 carbon atoms, a cycloalkyl group having 3 to 8 carbon atoms, an alkoxy group having 1 to 6 carbon atoms, an amino group, a substituted amino group, a heterocyclic group having 3 to 8 carbon atoms, a cyano group, a nitro group, or a halogen atom. Specific examples of the substituent include those described above.

A suitable ring includes a ring represented by Formula (X4) below.

[Chem. 9]

(X4)

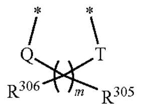

In Formula (X4), Q and T are each independently a sulfur atom, a substituted methylene group, an oxygen atom, or a group represented by $NR^{307}$. $R^{307}$ is a hydrogen atom, a hydroxyl group, an alkyl group, a haloalkyl group, a cycloalkyl group, an alkoxy group, an optionally substituted aryl group, an optionally substituted heteroaryl group, or a group represented by Formula (2).

$R^{305}$ and $R^{306}$ are each independently preferably a hydroxy group, an alkyl group, a haloalkyl group, a cycloalkyl group, an alkoxy group, an amino group, a substituted amino group, an optionally substituted heterocyclic group, a cyano group, a nitro group, a formyl group, a hydroxycarbonyl group, an alkylcarbonyl group, an alkoxycarbonyl group, a halogen atom, an optionally substituted aralkyl group, an optionally substituted aralkoxy group, an optionally substituted aryl group, a thiol group, an alkylthio group, an alkoxyalkylthio group, a haloalkylthio group, a cycloalkylthio group, or an optionally substituted arylthio group.

In addition, $R^{305}$ and $R^{306}$ may be taken together with a carbon atom to which they are attached to form an aliphatic ring that may have a substituent. Specific examples of the aliphatic ring include a cyclopentane ring, a cyclohexane ring, or the like. The substituent on the aliphatic ring is not particularly limited, but examples include a substituent selected from a hydroxyl group, an alkyl group, a haloalkyl group, a cycloalkyl group, an alkoxy group, an amino group, a substituted amino group, a heterocyclic group, a cyano group, a nitro group, or a halogen atom, in which 1 to 8 hydrogen atoms, especially preferably 1 to 4 hydrogen atoms in a group forming the ring are substituted with the substituent. Specific examples of the substituent will be described below.

In the formula above, m is an integer of 1 to 4.

<Group represented by Formula (X)>

[Chem. 10]

(X)

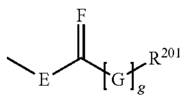

In Formula (X), E is an oxygen atom or $NR^{101}$. $R^{101}$ is a hydrogen atom or an alkyl group. E is $NR^{101}$ in which $R^{101}$ is preferably a hydrogen atom or an alkyl group having 1 to 6 carbon atoms.

F is an oxygen atom or a sulfur atom. F is preferably an oxygen atom.

G is an oxygen atom, a sulfur atom, or $NR^{202}$. $R^{202}$ is a hydrogen atom, an alkyl group, a cycloalkyl group, an aryl group, or a heteroaryl group. G is preferably NH.

g is 0 or 1.

$R^{201}$ is a hydrogen atom, an alkyl group, a cycloalkyl group, an aryl group, or a heteroaryl group. When G is an oxygen atom or a sulfur atom, $R^{201}$ is a group other than a hydrogen atom. $R^{201}$ is preferably an alkyl group having 1 to 6 carbon atoms, an alkoxy group having 1 to 6 carbon atoms, or an aryl group having 6 to 12 carbon atoms.

A suitable group represented by Formula (X) is as follows:

[Chem. 11]

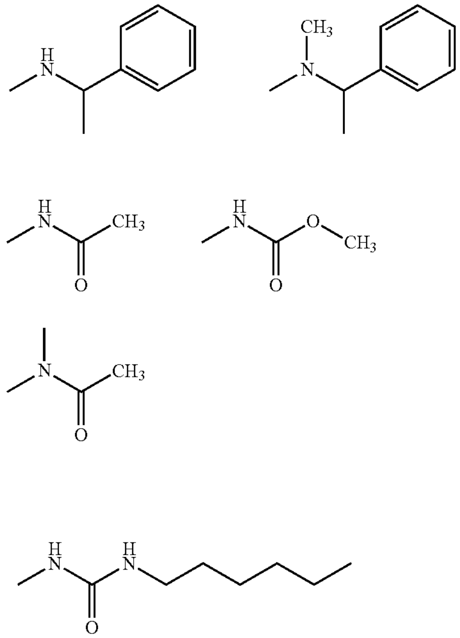

<Group represented by $L^1$-$R^{400}$>

In $L^1$-$R^{400}$, $R^{400}$ is a hydrogen atom, an alkyl group, an aryl group, a polymerizable group, a photochromic group, or a silyl group having an alkyl group, an alkoxyl group, or an aryl group as a substituent.

$L^1$ is a group represented by Formula (X2) below:

[Chem. 12]

(X2)

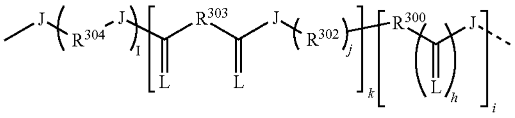

In Formula (X2), J is a divalent group. A plurality of Js are each independently directly attached, a substituted methylene group, an oxygen atom, a sulfur atom, or $NR^{301}$. $R^{301}$ is a hydrogen atom or an alkyl group. $R^{301}$ is preferably an alkyl group having 1 to 20 carbon atoms. The alkyl group preferably has a silyl group having an alkyl group having 1 to 10 carbon atoms, a polymerizable group, or a photochromic group as a substituent.

Examples of the polymerizable group include a radical polymerizable group such as a vinyl group, a 1-chlorovinyl group, an allyl group, a styryl group, a (meth)acryl group, a 2-(methacryloxy)ethylcarbamyl group, a 2-(methacryloxy)ethoxycarbonyl group, or a crotyl group, as well as an epoxy group, an episulfide group, a thietanyl group, an OH group, an SH group, an $NH_2$ group, a COOH group, an NCO group, or an NCS group, with a (meth)acrylic group, a 2-(methacryloxy)ethylcarbamyl group, a 2-(methacryloxy)ethoxycarbonyl group, an epoxy group, an OH group, an SH group, an $NH_2$ group, or a COOH group being preferred.

As a representative example, the photochromic group is exemplified by naphthopyran, spirooxazine, spiropyran, fulgide, fulgimide, or diarylethene. Indenonaphthopyran is preferred from the viewpoint of its ability to develop an excellent photochromic property, and indeno[2,1-f]naphtho[1,2-b]pyran is particularly preferred.

Indeno[2,1-f]naphtho[1,2-b]pyran is preferably a group represented by Formula (X3) below:

[Chem. 13]

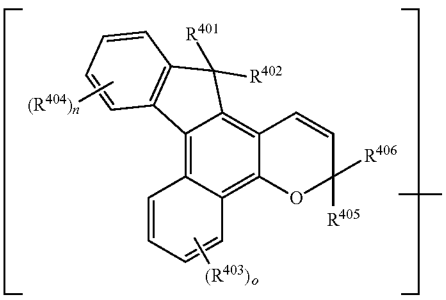

(X3)

In Formula (X3), $R^{401}$ and $R^{402}$ are each independently of $L^1$, a hydrogen atom, a hydroxyl group, an alkyl group, a haloalkyl group, a cycloalkyl group, an alkoxy group, an alkoxyalkyl group, a formyl group, a hydroxycarbonyl group, an alkylcarbonyl group, an alkoxycarbonyl group, a halogen atom, an optionally substituted aralkyl group, an optionally substituted aralkoxy group, an optionally substituted aryloxy group, or an optionally substituted aryl group, or a group represented by Formula (2).

$R^{401}$ and $R^{402}$ may be taken together with a carbon atom at position 13 to which they are attached to form an aliphatic ring having 3 to 20 ring member carbon atoms, a fused polycyclic ring in which an aromatic ring or an aromatic heterocyclic ring is fused to the above-mentioned aliphatic ring, a heterocyclic ring having 3 to 20 ring member atoms, or a fused polycyclic ring in which an aromatic ring or aromatic heterocyclic ring is fused to the above-mentioned heterocyclic ring. These rings may each have a substituent.

$R^{403}$ and $R^{404}$ are each independently $L^1$, a hydroxyl group, an alkyl group, a haloalkyl group, an optionally substituted cycloalkyl group, an alkoxy group, an amino group (including a primary or secondary amine group), a (optionally substituted) heterocyclic group having a nitrogen atom as a ring member and attached via the nitrogen atom to a carbon atom to which it is attached, a cyano group, a nitro group, a formyl group, a hydroxycarbonyl group, an alkylcarbonyl group, an alkoxycarbonyl group, a halogen atom, an optionally substituted aralkyl group, an optionally substituted aralkoxy group, an optionally substituted aryloxy group, an optionally substituted aryl group, an alkylthio group, a cycloalkylthio group, an optionally substituted arylthio group, or the group represented by Formula (2) above.

For $R^{403}$ and $R^{404}$, each independently, adjacent two may be taken together to form an (optionally substituted) aliphatic ring optionally including an oxygen atom, a nitrogen atom, or a sulfur atom.

$R^{405}$ and $R^{406}$ are each independently an optionally substituted aryl group or an optionally substituted heteroaryl group.

o is an integer of 0 to 4.

n is an integer of 0 to 4.

When o is 2 to 4, a plurality of $R^{403}$s may be the same as or different from each other.

When n is 2 to 4, a plurality of $R^{404}$s may be the same as or different from each other.

At least one of substituents on the aryl group or the heteroaryl group for $R^{401}$, $R^{402}$, $R^{403}$, $R^{404}$, and $R^{405}$ is attached to $L^1$.

A particularly suitable group represented by Formula (X2) is represented by any of the following formulae:

[Chem. 14]

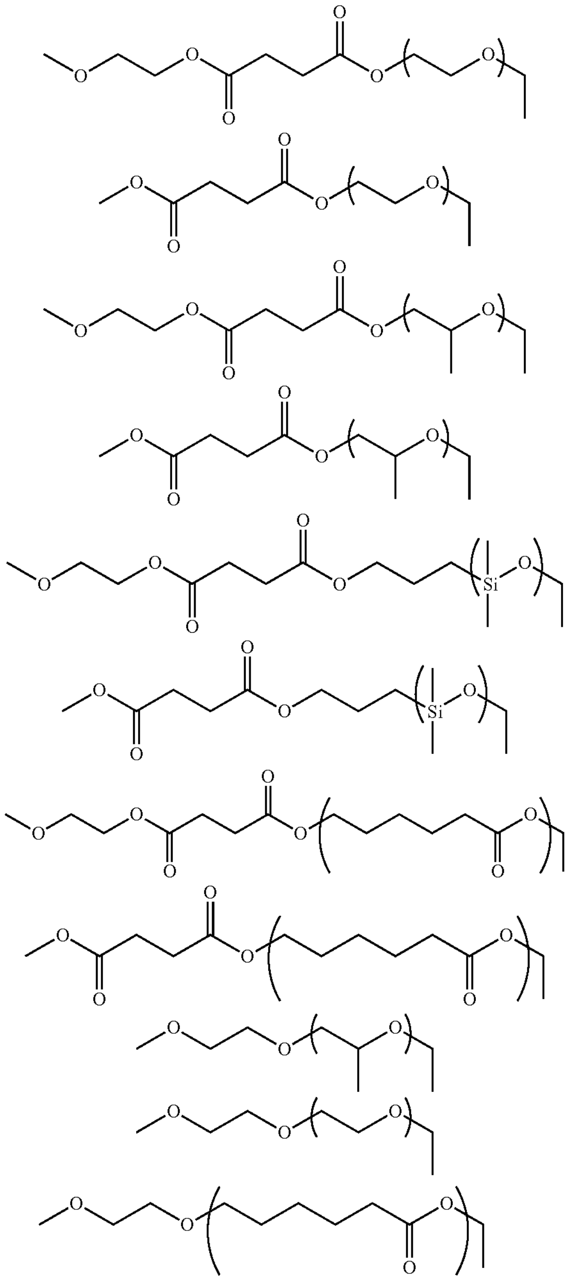

-continued

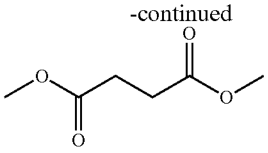

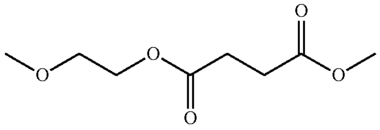

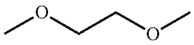

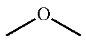

In Formula (X2), L is an oxygen atom or a sulfur atom.

$R^{300}$ is an alkylene group, or a silylene group having an alkyl group or an aryl group as a substituent. $R^{300}$ is preferably an alkylene group having 1 to 6 carbon atoms or a silylene group having an alkyl group having 1 to 6 carbon atoms as a substituent.

$R^{302}$, $R^{303}$, and $R^{304}$ are each independently an alkylene group. $R^{302}$ is preferably an alkylene group having 1 to 6 carbon atoms. $R^{303}$ is preferably an alkylene group having 1 to 6 carbon atoms. $R^{304}$ is preferably an alkylene group having 1 to 6 carbon atoms.

h, j, k, and l are an integer of 0 or 1.

i is an integer of 1 to 200. A plurality of units i may be the same as or different from each other.

i is preferably 5 to 100, more preferably 8 to 75, and most preferably 10 to 70.

A dashed line represents an attachment to $R^{400}$.

<Group represented by Formula (Y)>

$$-Q^1-(X^1Q^2)a-X^2Q^3 \quad (Y)$$

In Formula (Y), $Q^1$ is an alkylene group optionally including a halogen atom as a substituent. The alkylene group has preferably 1 or more and 20 or less carbon atoms, more preferably 1 or more and 12 or less carbon atoms, further preferably 1 or more and 7 or less carbon atoms, and most preferably 2 or more and 6 or less carbon atoms.

At least one halogen atom selected from the group consisting of I, Cl, Br, and F may be used. The halogen atom is preferably at least one of C1 or F and more preferably F.

$Q^2$ is an alkylene group optionally including a halogen atom as a substituent. A preferred aspect of a number of carbon atoms in the alkylene group and the halogen atom are the same as for $Q^1$. The number of carbon atoms in the alkylene group for $Q^2$ may be the same as or different from that of the alkylene group for $Q^1$.

$Q^3$ is an alkyl group optionally including a halogen atom as a substituent. The alkyl group has preferably 1 or more and 20 or less carbon atoms, more preferably 1 or more and 12 or less carbon atoms, and most preferably 1 or more and 7 or less carbon atoms. $Q^3$ may be a linear alkyl group or a branched alkyl group. $Q^3$ is preferably a linear alkyl group.

$X^1$ and $X^2$ are each independently O, S, $NR^{700}$, $PR^{701}$, or P(=O). $X^1$ and $X^2$ are each preferably O, S, or $NR^{700}$, more preferably O or S, and most preferably O.

$R^{700}$ is a hydrogen atom, an optionally substituted alkyl group, an optionally substituted cycloalkyl group, an optionally substituted aryl group, or an optionally substituted heteroaryl group, with a hydrogen atom, an optionally substituted alkyl group, or an optionally substituted aryl group being preferred. The alkyl group is preferably a methyl group, an ethyl group, a propyl group, a butyl group, or a pentyl group. The aryl group is preferably a phenyl group or a naphthyl group.

$R^{701}$ is a hydrogen atom, an optionally substituted alkyl group, an optionally substituted cycloalkyl group, an optionally substituted aryl group, or an optionally substituted heteroaryl group, with a hydrogen atom, an optionally substituted alkyl group, or an optionally substituted aryl group being preferred. The alkyl group is preferably a methyl group, an ethyl group, a propyl group, a butyl group, or a pentyl group. The aryl group is preferably a phenyl group or a naphthyl group.

Specific examples of the group represented by Formula (Y) include $-CH_2OCH_3$, $-CH_2SCH_3$, $-CH_2CH_2OCH_3$, $-CH_2CH_2OCH_2CH_3$, $-CH_2CH_2SCH_3$, $-CH_2CH_2CH_2OCH_3$, $-CH_2CH_2CH_2SCH_3$, $-CH_2CH_2OCH_2CH_2OCH_3$, $-CH_2CH_2OCH_2CH_2OCH_2CH_3$, or $-CH_2CH_2N(CH_3)_2$.

<$R^5$ and $R^6$>

In Formula (4), $R^5$ and $R^6$ are each independently an optionally substituted aryl group or an optionally substituted heteroaryl group.

$R^5$ and $R^6$ are each independently an optionally substituted phenyl group, an optionally substituted 1-naphthyl group, an optionally substituted 2-naphthyl group, an optionally substituted thienyl group, an optionally substituted furyl group, an optionally substituted pyrrolinyl group, an optionally substituted pyridyl group, an optionally substituted benzothienyl group, an optionally substituted benzofuranyl group, or an optionally substituted benzopyrrolinyl group. Furthermore, it is preferred that at least one, preferably both of $R^5$ and $R^6$ be an optionally substituted phenyl group, and it is more preferred that $R^5$ and $R^6$ both be substituted phenyl groups.

A substituent that the phenyl group has is preferably a hydroxyl group, an alkyl group, a haloalkyl group, an optionally substituted cycloalkyl group, an alkoxy group, an amino group, a substituted amino group, an optionally substituted heterocyclic group, a cyano group, a halogen atom, an alkylthio group, an optionally substituted arylthio group, a nitro group, a formyl group, a hydroxycarbonyl group, an alkylcarbonyl group, an alkoxycarbonyl group, an optionally substituted aralkyl group, an optionally substituted aralkoxy group, an optionally substituted aryloxy group, an optionally substituted aryl group, an optionally substituted heteroaryl group, a thiol group, an alkoxyalkylthio group, a haloalkylthio group, or an optionally substituted cycloalkylthio group, an optionally substituted silyl group, an optionally substituted oxysilyl group, the group represented by Formula (X), the group represented by $L^1$-$R^{400}$, or the group represented by Formula (Y). The substituent is more preferably an alkyl group, a haloalkyl group, an alkoxy group, an amino group, a substituted amino group, an optionally substituted heterocyclic group, a cyano group, a halogen atom, an alkylthio group, an optionally substituted arylthio group, an optionally substituted aryloxy group, an optionally substituted aryl group, an optionally substituted heteroaryl group, an alkoxyalkylthio group, a haloalkylthio group, an optionally substituted silyl group, an optionally substituted oxysilyl group, the group represented by $L^1$-$R^{400}$, or the group represented by Formula (Y)

Detailed Description of Substituents $R^3$, $R^4$, $R^5$, $R^6$, and substituents that they may include will be described in detail below. These substituents can be used as substituents that can be included in $R^{700}$ or $R^{701}$.

An alkyl group is not particularly limited, but is preferably an alkyl group having 1 to 6 carbon atoms. Suitable examples of the alkyl group having 1 to 6 carbon atoms include a methyl group, an ethyl group, an n-propyl group, an isopropyl group, an n-butyl group, a sec-butyl group, a tert-butyl group, a pentyl group, or a hexyl group.

A haloalkyl group is not particularly limited, but is preferably a haloalkyl group having 1 to 6 carbon atoms. The haloalkyl group having 1 to 6 carbon atoms is preferably an alkyl group substituted with a fluorine atom, a chlorine atom, or a bromine atom. Suitable examples of the haloalkyl group may include a trifluoromethyl group, a tetrafluoroethyl group, a chloromethyl group, a 2-chloroethyl group, a bromomethyl group, or a trifluoropropyl group.

A cycloalkyl group is not particularly limited, but is preferably a cycloalkyl group having 3 to 8 carbon atoms (cycloalkyl group in which 3 to 8 carbon atoms form a ring). Examples of the cycloalkyl group having 3 to 8 carbon atoms may include a cyclopropyl group, a cyclobutyl group, a cyclopentyl group, or a cyclohexyl group. Note that, the cycloalkyl group may have a substituent, but a number of carbon atoms (3 to 8 carbon atoms) shall not include a number of carbon atoms on the substituent.

An alkoxy group is not particularly limited, but is preferably an alkoxy group having 1 to 6 carbon atoms. Suitable examples of the alkoxy group having 1 to 6 carbon atoms include a methoxy group, an ethoxy group, an n-propoxy group, an isopropoxy group, an n-butoxy group, a sec-butoxy group, or a tert-butoxy group.

An amino group is a primary amino group ($-NH_2$). A substituted amino group is a secondary or tertiary amino group with one or two hydrogen atoms being substituted. A substituent that the substituted amino group has is not particularly limited, but includes an alkyl group having 1 to 6 carbon atoms, a haloalkyl group having 1 to 6 carbon atoms, an alkoxy group having 1 to 6 carbon atoms, a cycloalkyl group having 3 to 7 carbon atoms, an aryl group having 6 to 14 carbon atoms, or a heteroaryl group having 4 to 14 carbon atoms. Suitable examples of the amino group include an amino group, a methylamino group, a dimethylamino group, an ethylamino group, a diethylamino group, a phenylamino group, or a diphenylamino group.

A heterocyclic group preferably has 3 to 10 atoms. Specifically, for example, an aliphatic heterocyclic group such as a morpholino group, a piperidino group, a pyrrolidinyl group, a piperazino group, or an N-methylpiperazino group; or an aromatic heterocyclic group such as an indolinyl group can be used. Furthermore, the heterocyclic ring may have a substituent. The substituent is preferably an alkyl group having 1 to 6 carbon atoms. Suitable examples of a heterocyclic group having a substituent include a 2,6-dimethylmorpholino group, a 2,6-dimethylpiperidino group, or a 2,2,6,6-tetramethylpiperidino group.

Examples of a halogen atom include a fluorine atom, a chlorine atom, a bromine atom, or an iodine atom.

An alkylthio group is not particularly limited, but is preferably an alkylthio group having 1 to 6 carbon atoms. The alkylthio group having 1 to 6 carbon atoms may include a methylthio group, an ethylthio group, an n-propylthio group, an isopropylthio group, an n-butylthio group, a sec-butylthio group, or a t-butylthio group.

An arylthio group is not particularly limited, but is preferably an arylthio group having 6 to 10 carbon atoms. The arylthio group having 6 to 10 carbon atoms may include a phenylthio group, a 1-naphthylthio group, or a 2-naphthylthio group.

An alkylcarbonyl group is not particularly limited, but is preferably an alkylcarbonyl group having 2 to 7 carbon atoms. The alkylcarbonyl group having 2 to 7 carbon atoms may include an acetyl group or an ethylcarbonyl group.

An alkoxycarbonyl group is not particularly limited, but is preferably an alkoxycarbonyl group having 2 to 7 carbon atoms. The alkoxycarbonyl group having 2 to 7 carbon atoms may include a methoxycarbonyl group or an ethoxycarbonyl group.

An aralkyl group is not particularly limited, but is preferably an aralkyl group having 7 to 11 carbon atoms. The aralkyl group having 7 to 11 carbon atoms may include a benzyl group, a phenylethyl group, a phenylpropyl group, a phenylbutyl group, or a naphthylmethyl group.

An aralkoxy group is not particularly limited, but is preferably an aralkoxy group having 7 to 11 carbon atoms. The aralkoxy group having 7 to 11 carbon atoms may include a benzyloxy group or a naphthylmethoxy group.

An aryloxy group is not particularly limited, but is preferably an aryloxy group having 6 to 12 carbon atoms. The aryloxy group having 6 to 12 carbon atoms may include a phenyloxy group or a naphthyloxy group.

An aryl group is not particularly limited, but is preferably an aryl group having 6 to 12 carbon atoms. The aryl group having 6 to 12 carbon atoms may include a phenyl group, a 1-naphthyl group, or a 2-naphthyl group.

A heteroaryl group is not particularly limited, but is preferably a heteroaryl group having 3 to 12 carbon atoms. The heteroaryl group having 3 to 12 carbon atoms may include a thienyl group, a furyl group, a pyrrolinyl group, a pyridyl group, a benzothienyl group, a benzofuranyl group, or a benzopyrrolinyl group.

An alkoxyalkylthio group is not particularly limited, but is preferably an alkoxyalkylthio group having 2 to 9 carbon atoms. The alkoxyalkylthio group having 2 to 9 carbon atoms may include a methoxymethylthio group, a methoxyethylthio group, a methoxy n-propylthio group, a methoxy n-butylthio group, an ethoxytehylthio group, or an n-propoxypropylthio group.

A haloalkylthio group is not particularly limited, but is preferably a haloalkylthio group having 1 to 6 carbon atoms. The haloalkylthio group having 1 to 6 carbon atoms may include a trifluoromethylthio group, a tetrafluoroethylthio group, a chloromethylthio group, a 2-chloroethylthio group, or a bromomethylthio group.

A cycloalkylthio group is not particularly limited, but is preferably a cycloalkylthio group having 3 to 8 carbon atoms. The cycloalkylthio group having 3 to 8 carbon atoms may include a cyclopropylthio group, a cyclobutylthio group, a cyclopentylthio group, or a cyclohexylthio group. Notably, it is noted that the cycloalkylthio group may have a substituent, but a number of carbon atoms (3 to 8 carbon atoms) shall not include a number of carbon atoms on the substituent.

A silyl group may have a substituent. A substituent that a substituted silyl group has is not particularly limited, but includes an alkyl group having 1 to 6 carbon atoms, a haloalkyl group having 1 to 6 carbon atoms, an alkoxy group having 1 to 6 carbon atoms, a cycloalkyl group having 3 to 7 carbon atoms, an aryl group having 6 to 14 carbon atoms, or a heteroaryl group having 4 to 14 carbon atoms.

An oxysilyl group may have a substituent. A substituent that a substituted oxysilyl group has is not particularly limited, but includes an alkyl group having 1 to 6 carbon atoms, a haloalkyl group having 1 to 6 carbon atoms, an alkoxy group having 1 to 6 carbon atoms, a cycloalkyl group having 3 to 7 carbon atoms, an aryl group having 6 to 14 carbon atoms, or a heteroaryl group having 4 to 14 carbon atoms.

Note that, the cycloalkyl group, the arylthio group, the aralkyl group, the aralkoxy group, the aryloxy group, the aryl group, the heteroaryl group, and the cycloalkylthio group may be unsubstituted. However, when the above-mentioned groups are substituted, 1 to 8 hydrogen atoms, especially preferably 1 to 4 hydrogen atoms in a ring-forming group are preferably substituted by a substituent selected from a hydroxyl group, an alkyl group having 1 to 6 carbon atoms, a haloalkyl group having 1 to 6 carbon atoms, a cycloalkyl group having 3 to 8 carbon atoms, an alkoxy group having 1 to 6 carbon atoms, an amino group, a substituted amino group, a heterocyclic group having 3 to 8 atoms, a cyano group, a nitro group, or a halogen atom. Specific examples of these substituents are the same groups as described above.

<Photochromic Compound Represented by Formula (4)>

A particularly suitable chromene compound includes a compound represented by Formula (4) below:

[Chem. 15]

(4)

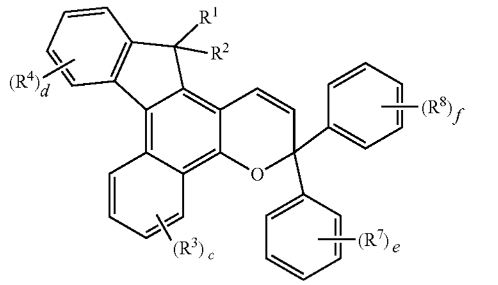

In Formula (4), $R^1$, $R^2$, $R^3$, $R^4$, c, and d are the same as in Formula (3).

<$R^7$ and $R^8$>

$R^7$ and $R^8$ are a hydroxyl group, an alkyl group having 1 to 6 carbon atoms, a haloalkyl group having 1 to 6 carbon atoms, a cycloalkyl group having 3 to 8 carbon atoms, an alkoxy group having 1 to 6 carbon atoms, an amino group, a heterocyclic group, a cyano group, a halogen atom, an alkylthio group having 1 to 6 carbon atoms, or an optionally substituted arylthio group having 6 to 10 carbon atoms, or $L^1$-$R^{400}$.

e denotes a number of $R^7$ and an integer of 0 to 5. When e is 2 or more, $R^7$s may be the same as or different from each other.

When e is 2 to 5 and adjacent $R^7$s are present, two adjacent $R^7$s may be taken together with a carbon atom to which $R^7$s are attached to form a ring optionally including an oxygen atom, a sulfur atom, a carbon atom, or a nitrogen atom and the ring is optionally substituted. Note that, the ring can also simultaneously have two or more atoms of an oxygen atom, a sulfur atom, a carbon atom, or a nitrogen atom.

f denotes a number of $R^8$ and an integer of 0 to 5. When f is 2 or more, $R^8$s may be the same as or different from each other.

When f is 2 to 5 and adjacent $R^8$s are present, two adjacent $R^8$s may be taken together with a carbon atom to which $R^8$s are attached to form a ring optionally including an oxygen atom, a sulfur atom, a carbon atom, or a nitrogen atom and the ring is optionally substituted. Note that, the ring can also simultaneously have two or more atoms of an oxygen atom, a sulfur atom, a carbon atom, or a nitrogen atom.

For $R^7$ and $R^8$, each independently, adjacent two may be taken together to form a ring group optionally including an oxygen atom, a sulfur atom, a carbon atom, or a nitrogen atom. This ring group is not particularly limited, but is preferably a ring having 5 to 8 atoms including a carbon atom to which $R^7$ and $R^8$ are attached. The ring may have a substituent. However, the substituent may be a substituent selected from a hydroxyl group, an alkyl group having 1 to 6 carbon atoms, a haloalkyl group having 1 to 6 carbon atoms, a cycloalkyl group having 3 to 8 carbon atoms, an alkoxy group having 1 to 6 carbon atoms, an amino group, a substituted amino group, a heterocyclic group having 3 to 8 carbon atoms, a cyano group, a nitro group, or a halogen atom. Specific examples of these substituents are the same groups as described above. For the ring, it is preferred that a plurality of the rings be taken together to form the ring represented by Formula (X4).

Specific Example of Suitable Photochromic Compound

Specific examples of a particularly suitable photochromic compound include photochromic compounds represented by formulae below.

[Chem. 16]

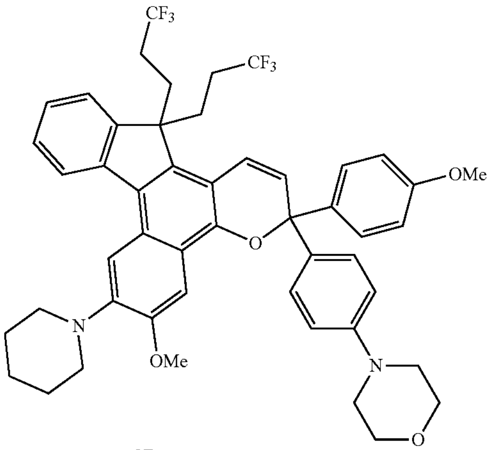

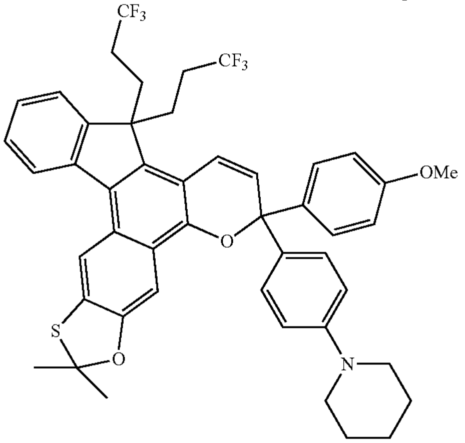

-continued
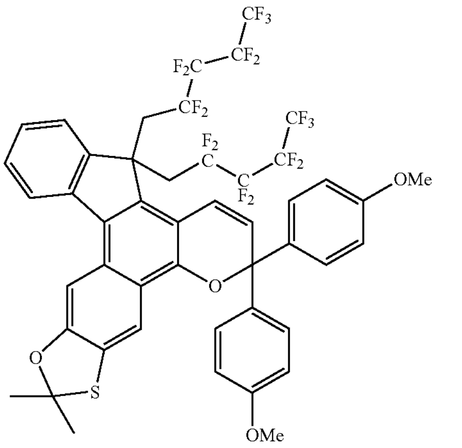
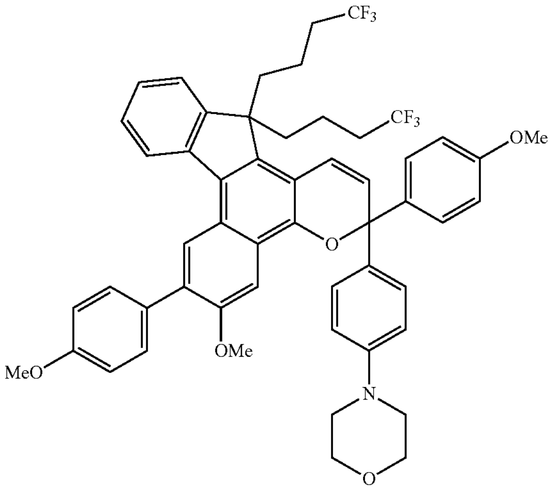
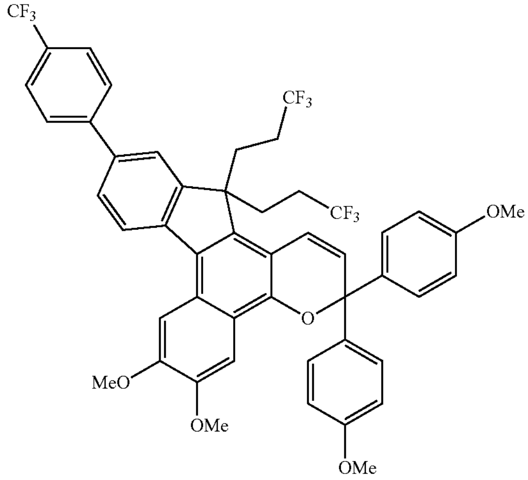
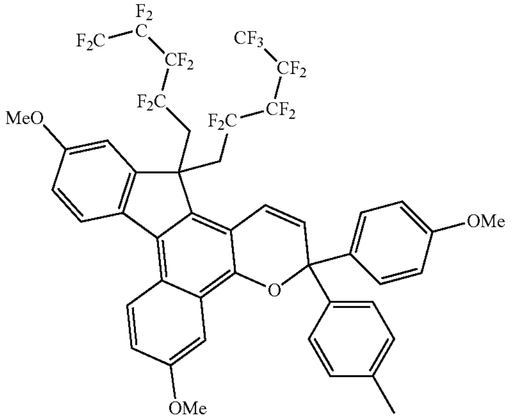
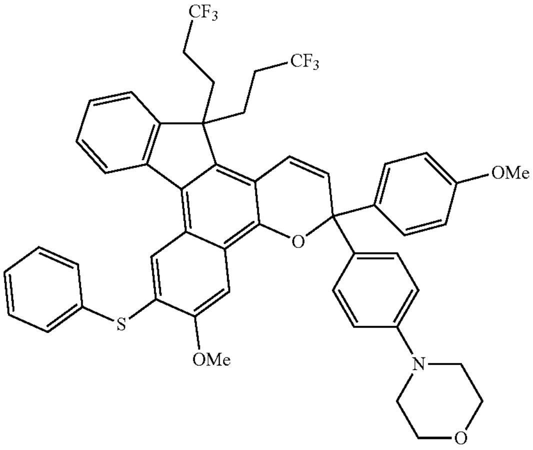
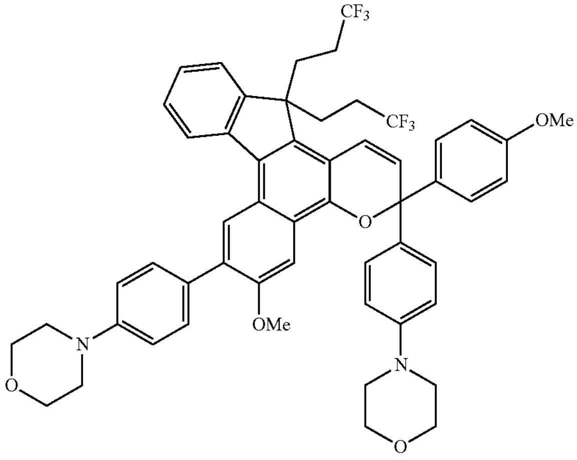

-continued

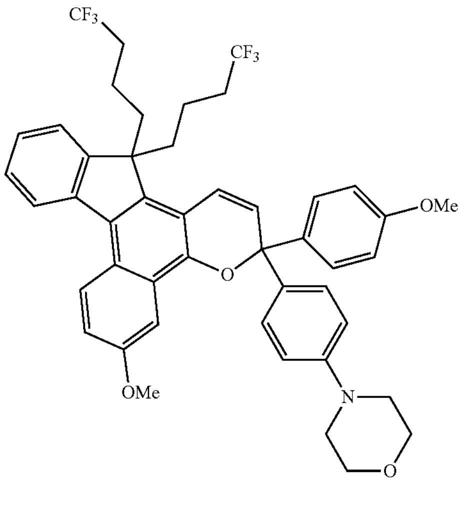

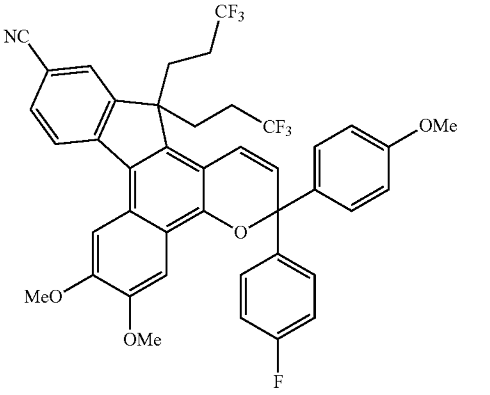

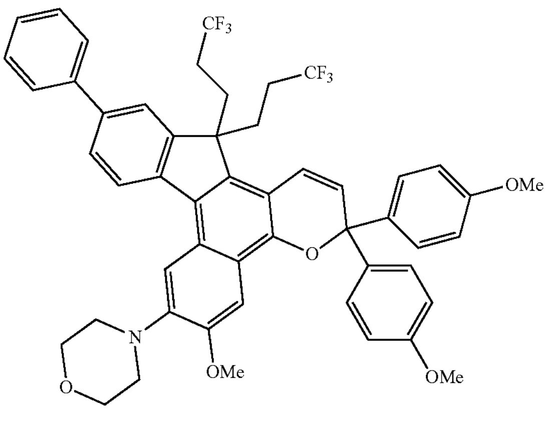

-continued

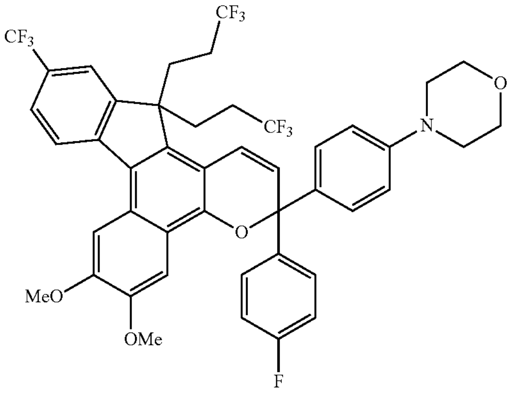

[Naphthol Derivative]

A naphthol derivative according to the embodiment has a backbone represented by Formula (5) below. The naphthol derivative can be used as an intermediate for synthesizing a photochromic compound having a backbone represented by Formula (1) above.

[Chem. 17]

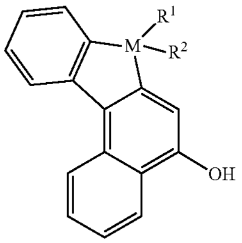

(5)

In Formula (5), M, $R^1$, and $R^2$ are each independently the same as in Formula (1) above.

<Naphthol Derivative Represented by Formula (6)>

A naphthol derivative represented by Formula (6) can be used as an intermediate for synthesizing a naphthol derivative represented by Formula (3) or (4) above.

[Chem. 18]

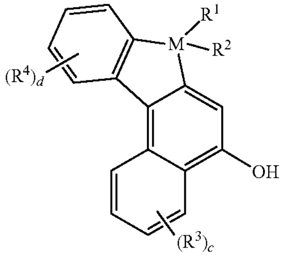

(6)

In Formula (6), M, $R^1$, and $R^2$ are each independently the same as in Formula (1) above. $R^3$, $R^4$, c, and d are each independently the same as in Formula (3) above.

Specific Examples of Naphthol Derivative
Specific examples of a naphthol derivative according to the embodiment include a compound represented by any of the following formulae:
[Chem. 19]
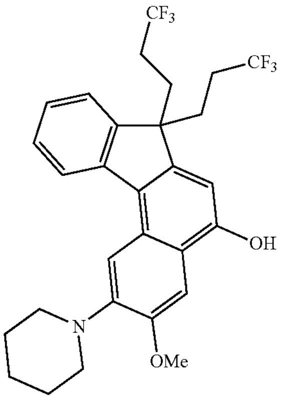
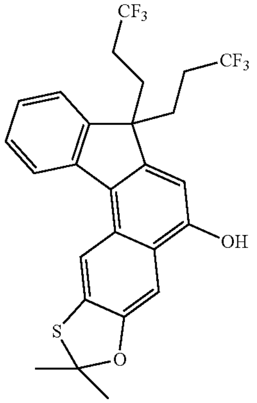
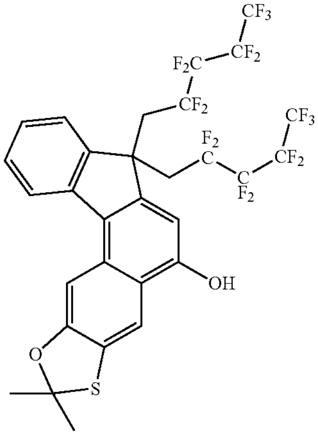
-continued
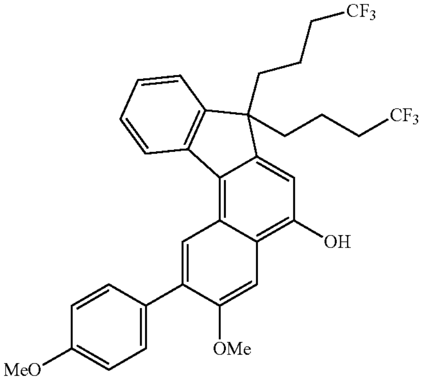
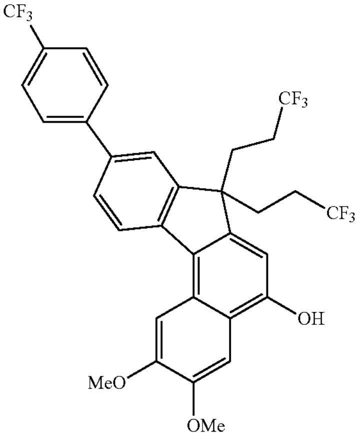
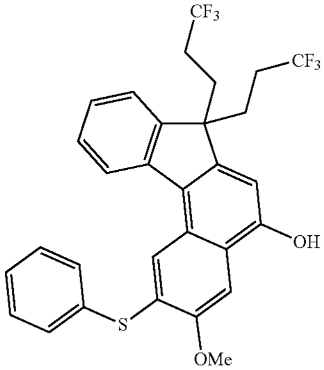
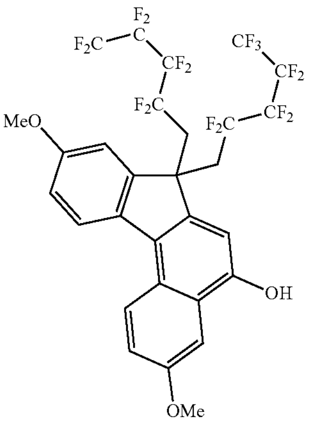

-continued

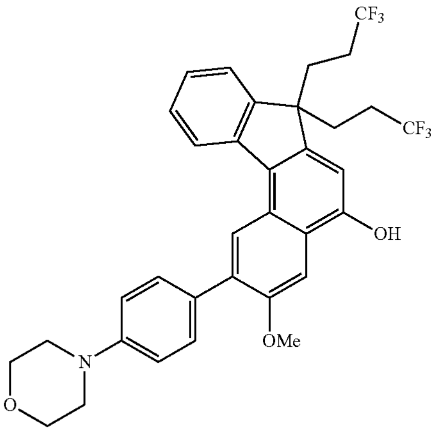

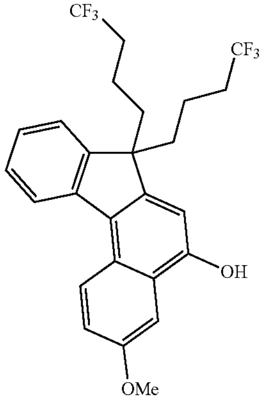

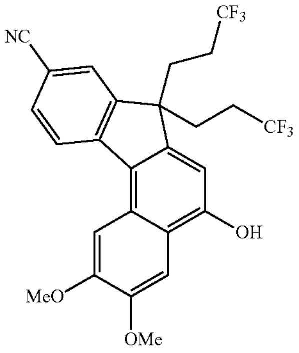

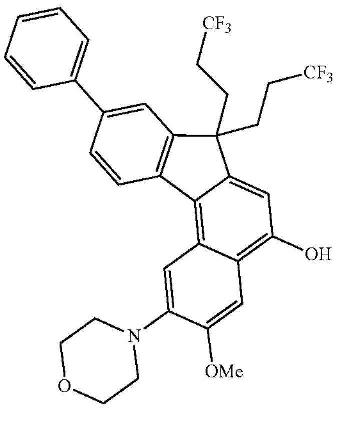

-continued

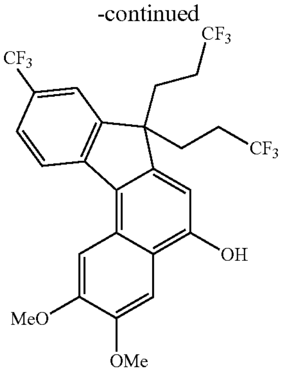

[Method for Producing Photochromic Compound]

A photochromic compound according to the embodiment may be produced by any synthetic method. Representative examples of a method for producing a photochromic compound will be described, but the method is not limited thereto. Note that, in the following description, a symbol in each formula has the same meaning as described for any of the above-mentioned formulae, unless otherwise noted.

A photochromic compound may be produced by a method in which the naphthol derivative represented by Formula (6) and a propargyl alcohol compound represented by Formula (7) below:

[Chem. 20]

(7)

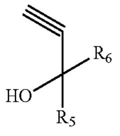

are reacted in the presence of an acid catalyst. In Formula (7), $R^5$ and $R^6$ are each independently the same as in Formula (3) above.

A reaction ratio of a naphthol compound to the propargyl alcohol compound is preferably selected from a range of 1:10 to 10:1 (molar ratio). For example, sulfuric acid, benzene sulfonic acid, p-toluenesulfonic acid, acidic alumina, or the like are used as the acid catalyst. The acid catalyst is preferably used in a range of 0.1 to 10 parts by weight per 100 parts by weight of a total of the naphthol compound and the propargyl alcohol compound. A reaction temperature is preferably 0 to 200° C. A solvent is preferably a non-protic organic solvent such as N-methylpyrrolidone, dimethylformamide, tetrahydrofuran, benzene, toluene, or the like. A method for purifying a product obtained from such a reaction is not particularly limited. For example, the product can be purified by silica gel column purification and then recrystallization.

<Method for Synthesizing Naphthol Derivative>

A naphthol derivative can be synthesized based on any of reaction methods described in, for example, Non-Patent Document 1, Non-Patent Document 2, or Patent Document 4.

A method for synthesizing the naphthol compound represented by Formula (6) above is not particularly limited. For example, when M is a carbon atom, the naphthol compound can be synthesized as follows.

First, a benzene compound represented by Formula (8) below is reacted with an acid chloride represented by Formula (9) below to obtain a compound represented by Formula (10) below. Note that, in Formula (10) above, $R^3$, $R^4$, c, and d are the same as in Formula (3) above.

[Chem. 21]

(8)

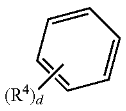

[Chem. 22]

(9)

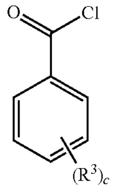

[Chem. 23]

(10)

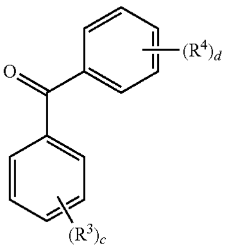

Furthermore, the compound (10) is subjected to a Stobbe reaction, a cyclization reaction, a hydrolysis reaction using an alkali or acid, benzyl protection, or debenzylation by a hydrolysis reaction using an alkali or an acid to obtain a carboxylic acid of which hydroxyl group is protected with benzyl (Bn) as represented by Formula (11) below. The thus-benzyl-protected carboxylic acid represented by Formula (11) above is then converted to an amine by Curtius rearrangement, Hofmann rearrangement, Lossen rearrangement, or the like, and a diazonium salt is prepared from the amine. The diazonium salt is converted to a halide such as a bromide or an iodide by a Sandmeyer reaction, or the like to obtain a halide represented by Formula (12) below in which Hal represents a halogen.

[Chem. 24]

(11)

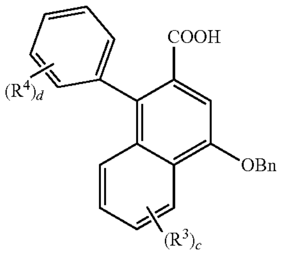

-continued

[Chem. 25]

(12)

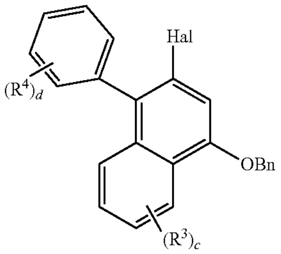

The thus-obtained halide is reacted with magnesium, lithium, or the like to prepare an organometallic reagent. This organometallic reagent is reacted with a ketone represented by Formula (13) below in which $R^1$ and $R^2$ are the same as in Formula (3) above in an organic solvent at −100 to 70° C. to obtain a compound represented by Formula (14) below.

[Chem. 26

(13)

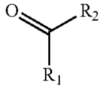

[Chem. 27]

(14)

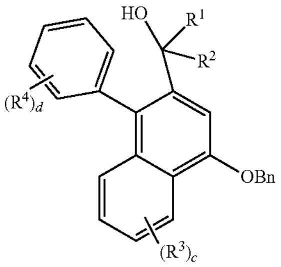

The thus-obtained compound (14) is debenzylated and then reacted under a neutral to acidic condition at 10 to 120° C. for 10 minutes to 2 hours to thereby convert alcohol into its spiro form. Thus, a desired naphthol derivative represented by Formula (6) above can be synthesized. In such a reaction, a reaction ratio of the organometallic reagent to the ketone represented by Formula (13) may be selected from a wide range, but preferably from a range of 1:10 to 10:1 (molar ratio). A reaction temperature is preferably −100 to 70° C. A non-protic organic solvent such as diethyl ether, tetrahydrofuran, benzene, or toluene is preferably used as the solvent. The conversion of the alcohol into its spiro form under a neutral to an acidic condition is preferably performed in the presence of an acid catalyst. For example, acetic acid, hydrochloric acid, sulfuric acid, benzene sulfonic acid, p-toluenesulfonic acid, acidic alumina, or the like is used as the acid catalyst. Such an acid catalyst is suitably used in a range of 0.1 to 10 parts by weight per 100 parts by weight of the alcohol. The alcohol is preferably converted into its spiro form in the presence of a solvent such as tetrahydrofuran, benzene, or toluene.

The above-mentioned method is suitably used for synthesizing a photochromic compound in which $R^1$ and $R^2$ are different from each other. The above-mentioned method is also suitably used when $R^1$ and $R^2$ are the same as each other, but another method can also be used. Another method alternative to the above-mentioned method will be described below.

First, a carboxylic acid compound represented by Formula (15) below, which is obtained by subjecting the compound of Formula (10) to a Stobbe reaction, a cyclization reaction, or a hydrolysis reaction using an alkali or acid, is converted into its spiro form under a neutral to acidic condition and reduced using hydrogen or hydrazine to obtain a naphthol derivative represented by Formula (16) below.

[Chem. 28]

(15)

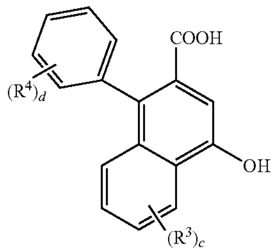

[Chem. 29]

(16)

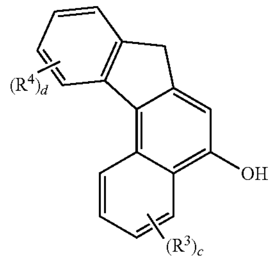

A hydroxyl group in the thus-obtained naphthol derivative is protected by benzyl protection, acetal protection, silyl protection, or the like to obtain a compound of Formula (17) below in which OPro denotes a protected hydroxyl group.

[Chem. 30]

(17)

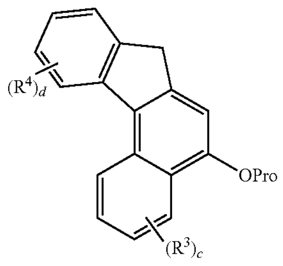

The compound can be reacted with a halide of $R^1$ under a basic condition, followed by deprotection to obtain a compound represented by Formula (18) below, which is a compound represented by Formula (6) above in which $R^1$=$R^2$.

[Chem. 31)

(18)

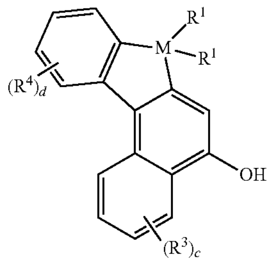

Another method alternative to the above-mentioned method, the compound represented by Formula (17) can also be synthesized by intramolecular cyclization of a halogen compound of Formula (13) above in the presence of a palladium catalyst.

<Method for Synthesizing Naphthol Derivative Including Si or Ge>

One exemplary method for producing a naphthol derivative represented by Formula (6) in which M is Si or Ge will be described.

First, the halide represented by Formula (12) is reacted with magnesium, lithium, or the like to prepare an organometallic reagent. This organometallic reagent is reacted with a monohalide represented by Formula (19) below in which $R^1$ and $R^2$ are the same as in Formula (3) above in an organic solvent at −100 to 70° C. to obtain a compound represented by Formula (20) below.

[Chem. 32]

(19)

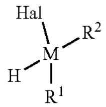

[Chem. 33]

(20)

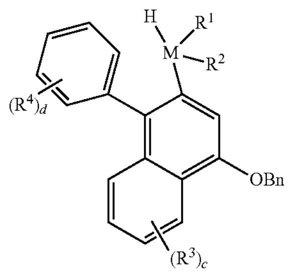

The thus-obtained compound (20) is cyclized to obtain a cyclized form represented by Formula (21) below with reference to any of reaction methods described in Non-Patent Document 3, Non-Patent Document 4, Patent Document 5, or the like.

[Chem. 34]

(21)

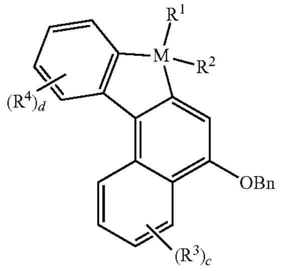

The thus-obtained cyclized form can be debenzylated to obtain the naphthol derivative of Formula (6).

<Identification of Photochromic Compound>

A photochromic compound according to the embodiment is, for example, a solid or viscous liquid at room temperature and normal pressure. A photochromic compound may be isolated from this solid or liquid by separation operations such as thin layer chromatography, silica gel column chromatography, high-performance liquid chromatography, gas chromatography, or the like. The absence of a byproduct such as a raw material compound or a coloring matter other than the photochromic compound is confirmed.

The thus-obtained photochromic compound is characterized by proton nuclear magnetic resonance spectroscopy ($^1$H-NMR) and a peak based on an aromatic proton and an alkene proton appears around δ: 5.0 to 9.0 ppm and a peak based on protons of an alkyl group and an alkylene group appears around δ: 1.0 to 4.0 ppm. By relatively comparing spectral intensities of the peaks, a number of protons on each attached group can be determined. This allows identification of a backbone, a substituent, or the like that the photochromic compound has.

When the photochromic compound is included in a cured product such as a resin, the photochromic compound can be isolated by dissolving the resin and using the above-mentioned separation operations.

<Photochromic Composition>

A photochromic compound according to the embodiment can be dissolved in a common organic solvent such as toluene, chloroform, or tetrahydrofuran. When the photochromic compound having a backbone represented by Formula (1) is dissolved in such a solvent, a clear, colorless solution is obtained. This solution exhibits good photochromic behavior, that is, when the solution is irradiated with sunlight or ultraviolet light, it quickly develops a color and when the sunlight or the like is blocked, it quickly reversibly returns to its original colorless state.

The photochromic compound according to the embodiment can be used in combination with a photochromic compound having another structure, depending on the intended use. For example, it can be used in combination with another photochromic compound in order to obtain various color tones required for a photochromic lens. A photochromic compound to be combined may be any known compound without any limitation. Examples thereof include indenonaphthopyran, naphthopyran, spirooxazine, spiropyran, fulgide, fulgimide, or diarylethene. Among them, an indenonaphthopyran compound is particularly preferred since it can maintain a uniform color tone upon color development and fading, can suppress a color shift upon color development associated with degradation of a photochromic property, and can reduce initial coloration. It is preferred to use a plurality of photochromic compounds according to the embodiment to adjust a color tone since they have a fast color fading rate and excellent durability.

When a photochromic composition including the photochromic compound according to the embodiment and another photochromic compound is produced, a blending ratio of the photochromic compounds is appropriately determined in accordance with a desired color tone.

<Photochromic Curable Composition>

A curable composition according to the embodiment includes a photochromic compound according to the embodiment; and at least one selected from the group consisting of a radical polymerizable monomer, a cationic polymerizable monomer, a compound having a polymerization reactive group, and a (thio)urethane(urea) polymer.

The photochromic compound according to the embodiment and the photochromic composition are preferably used in combination with a polymerizable compound as a photochromic curable composition.

For the photochromic curable composition, although it all depends on a color developing intensity of a photochromic compound, a lens material selected, and a thickness of a lens, the photochromic compound (or photochromic composition) is preferably used in an amount of 0.001 to 10 parts by mass relative to 100 parts by mass of the polymerizable compound. An optimal amount to be incorporated depends on application for which the photochromic curable composition is used. For example, the case where the photochromic curable composition is used as a thin-film optical article or as a thick-film optical article will be described below.

(Use as Thin-Film Optical Article)

For example, when a thin film of 10 μm or more and less than 1000 μm, e.g., about 100 μm (polymer film made by polymerization of the photochromic curable composition) is formed from the photochromic curable composition, 0.001 to 10 parts by mass of a photochromic compound (or photochromic composition) relative to 100 parts by mass of another polymerizable monomer may be used to adjust a color tone.

(Use as Thick Film Optical Article)

In the case of a thick cured product (polymeric molded product made by polymerization of the photochromic curable composition), e.g., a cured product having a thickness of 1 mm or more, 0.001 to 1 part by mass of a photochromic compound (or photochromic composition) relative to 100 parts by mass of the thick cured product or another polymerizable monomer that gives the thick cured product may be used to adjust a color tone.

<Polymerizable Compound>

As mentioned above, a photochromic compound is preferably used as a photochromic curable composition in combination with a polymerizable compound. Examples of the polymerizable compound may include a urethane- or urea-based polymerizable compound that can form a urethane bond or a urea bond, a compound having a polymerization reactive group, a radical polymerizable compound, an epoxy-based polymerizable compound, or the like. These polymerizable compounds are not particularly limited, but, for example, the polymerizable compound described in Patent Document 5 may be suitably used.

Among them, the below-mentioned polymerizable compounds are particularly suitably used.

<Compound Having Polymerization Reactive Group>

An example of a compound having a polymerization reactive group includes a compound having an iso(thio)cyanate group. An iso(thio)cyanate compound is a compound having an isocyanate group or an isothiocyanate group and may include both an isocyanate group and an isothiocyanate group. This compound is suitable for use in combination with an active hydrogen-containing compound as described below. Examples of such an iso(thio)cyanate compound include, but are not limited to, the below-mentioned compounds.

(Polyiso(thio)cyanate)

Polyiso(thio)cyanate is a compound having at least two or more iso(thio)cyanate groups per molecule. Examples of the polyiso(thio)cyanate include an aromatic polyiso(thio)cyanate having an aromatic ring such as m-xylene diisocyanate or 4,4'-diphenylmethane diisocyanate; or an aliphatic polyiso(thio)cyanate such as norbornane diisocyanate or dicyclohexylmethane-4,4'-diisocyanate.

(Active Hydrogen-Containing Compound)

An active hydrogen-containing compound is preferably a compound having a hydroxyl group and/or a thiol group and particularly preferably a polyfunctional compound having two or more active hydrogens per molecule, but is not limited thereto. Specific examples of the active hydrogen-containing compound may include a polyfunctional thiol compound such as pentaerythritol tetrakis(3-mercaptopropionate) or 4-mercaptomethyl-3,6-dithia-octanedithiol; or a polyfunctional alcohol such as trimethylolpropane or pentaerythritol.

(Radical Polymerizable Compound)

A radical polymerizable compound includes a polyfunctional radical polymerizable compound and a monofunctional radical polymerizable compound. Each of these can be used alone or a plurality of them can be used in combination. Examples of a radical polymerizable substituent include a group having an unsaturated double bond, i.e., a vinyl group (including a styryl group, a (meth)acryl group, an allyl group, or the like).

The polyfunctional radical polymerizable compound is a compound having two or more radical polymerizable substituents in a molecule. This polyfunctional radical polymerizable compound includes a first polyfunctional radical polymerizable compound having 2 to 10 radical polymerizable substituents and a second polyfunctional radical polymerizable compound having more than 10 radical polymerizable substituents.

The first radical polymerizable compound is not particularly limited, but more preferably has 2 to 6 radical polymerizable substituents. Specific examples thereof are as follows.

(Polyfunctional (Meth)Acrylic Acid Ester Compound)

Ethylene glycol di(meth)acrylate, diethylene glycol di(meth)acrylate, triethylene glycol di(meth)acrylate, tetraethylene glycol di(meth)acrylate, ethylene glycol bisglycidyl (meth)acrylate, bisphenol A di(meth)acrylate, 2,2-bis (4-(meth)acryloyloxyethoxyphenyl)propane, 2,2-bis(3,5-dibromo-4-(meth)acryloyl, oxyethoxyphenyl)propane.

(Polyfunctional Allyl Compound)

Diallyl phthalate, diallyl terephthalate, diallyl isophthalate, diallyl tartrate, diallyl epoxysuccinate, diallyl fumarate, diallyl chlorendate, diallyl hexaphthalate, diallyl carbonate, allyl diglycol carbonate, trimethylolpropane triallyl carbonate.

(Polyfunctional Thio(Meth)Acrylic Acid Ester Compound)

1,2-bis(methacryloylthio)ethane, bis(2-acryloylthioethyl) ether, 1,4-bis(methacryloylthiomethyl)benzene.

(Vinyl Compound)

Divinylbenzene.

Examples of the second polyfunctional radical polymerizable compound having more than 10 radical polymerizable substituents include a compound having a relatively large molecular weight such as a silsesquioxane compound having a radical polymerizable substituent or a polyrotaxane compound having a radical polymerizable substituent.

The monofunctional radical polymerizable compound is a compound having one radical polymerizable substituent in a molecule, and specific examples thereof include, but are not limited to, the below-mentioned compounds.

(Unsaturated Carboxylic Acid)

Acrylic acid, methacrylic acid, maleic anhydride.

((Meth)Acrylic Acid Ester)

Methyl (meth)acrylate, benzyl methacrylate, phenyl methacrylate.

2-Hydroxyethyl methacrylate, glycidyl (meth)acrylate, β-methyl glycidyl (meth)acrylate, bisphenol A-monoglycidyl ether methacrylate, 4-glycidyloxy methacrylate, 3-(glycidyl-2-oxyethoxy)-2-hydroxy, propyl methacrylate, 3-(glycidyloxy-1-isopropyloxy)-2-hydroxypropyl acrylate, 3-glycidyloxy-2-hydroxypropyloxy)-2-hydroxypropyl acrylate.

(Fumaric Acid Ester)

Diethyl fumarate, diphenyl fumarate.

(Thio(Meth)Acrylic Acid)

Methyl thioacrylate, benzyl thioacrylate, benzyl thiomethacrylate.

(Vinyl Compound)

Styrene, chlorostyrene, tylstyrene, vinylnaphthalene, α-methylstyrene dimer, bromostyrene.

The radical polymerizable compound may be used alone or a mixture of a plurality of types of them may also be used. In this case, preferably 80 to 100 parts by mass of the polyfunctional radical polymerizable compound and 0 to 20 parts by mass of the monofunctional radical polymerizable compound, and more preferably 90 to 100 parts by mass of the polyfunctional radical polymerizable compound and 0 to 10 parts by mass of the monofunctional radical polymerizable compound are used per 100 parts by mass of a total of the radical polymerizable compounds. Furthermore, preferably 80 to 100 parts by mass of the first polyfunctional radical polymerizable compound, 0 to 20 parts by mass of the second radical polymerizable compound, and 0 to 20 parts by mass of the monofunctional radical polymerizable compound, and further preferably 85 to 100 parts by mass of the first polyfunctional radical polymerizable compound, 0 to 10 parts by mass of the second polyfunctional radical polymerizable compound, and 0 to 10 parts by mass of the monofunctional radical polymerizable compound are used per 100 parts by mass of a total of the radical polymerizable compounds.

(Various Compounding Agents)

Various known compounding agents may be incorporated into a curable composition as long as the effect is not impaired. Examples of the compounding agent include, for example, a releasing agent, a UV absorber, an IR absorber, a UV stabilizer, an antioxidant, an anti-coloring agent, an antistatic agent, a fluorescent dye, a dye, a pigment, a perfume, and various other stabilizers. A solvent or a leveling agent can also be incorporated. A thiol such as t-dodecyl mercaptan can be incorporated as a polymerization regulator.

Among the above-mentioned compounding agents, the UV stabilizer is suitably used from the viewpoint of improving durability of a photochromic moiety. A hindered amine light stabilizer, a hindered phenol antioxidant, a sulfur antioxidant, or the like are known as such a UV stabilizer. A particularly suitable UV stabilizer is as follows:

Bis(1,2,2,6,6-pentamethyl-4-piperidyl)sebacate; ADK STAB LA-52, LA-57, LA-62, LA-63, LA-67, LA-77, LA-82, LA-87 (manufactured by ADEKA CORPORATION); 2,6-di-tert-butyl-4-methyl-phenol, ethylene bis(oxyethylene) bis[3-(5-tert-butyl-4-hydroxy-m-tolyl) propionate]; IRGANOX 1010, 1035, 1075, 1098, 1135, 1141, 1222, 1330, 1425, 1520, 259, 3114, 3790, 5057, 565 (manufactured by BASF Japan). An amount of such a UV stabilizer to be used is not particularly limited unless the effect is impaired, but is usually in a range of 0.001 to 10 parts by mass, especially 0.01 to 1 part by mass per 100 parts by mass of a photochromic curable composition.

A UV absorber may also be used in addition to the UV stabilizer. Known UV absorbers such as a benzophenone compound, a benzotriazole compound, a cyanoacrylate compound, a triazine compound, or a benzoate compound can be used as the UV absorber, with a cyanoacrylate compound or a benzophenone compound being particularly preferred. The above-mentioned UV stabilizer is preferably used in a range of 0.001 to 5 parts by mass relative to 100 parts by mass of a photochromic curable composition including a photochromic compound and a polymerizable compound.

<Method for Using Photochromic Curable Composition; Optical Article>

A photochromic curable composition is cured to obtain a photochromic cured product. Polymerization curing for producing the photochromic cured product is performed by radical polymerization, ring-opening polymerization, anionic polymerization, or condensation polymerization using irradiation with an active energy ray such as an ultraviolet ray, an α-ray, a β-ray, or a γ-ray; heat; or a combination thereof. In other words, an appropriate polymerization method may be employed depending on a type of a polymerizable compound or a polymerization accelerator and a form of a photochromic cured product to be formed.

When a curable composition containing a polymerizable compound is thermally polymerized, a temperature affects a property of the resulting photochromic cured product.

Such a temperature condition cannot be generally limited since it is affected by a type or amount of a thermal polymerization initiator or a type of polymerizable compound. However, in general, a method in which polymerization is started at a relatively low temperature, followed by heating slowly is suitable. Polymerization time also varies depending on various factors as is the case with the temperature. Therefore, although it is suitable to determine an optimum time in advance in accordance with these conditions, in general, the conditions are preferably selected so that polymerization is completed in 2 to 48 hours. When obtaining a photochromic laminated sheet, polymerization is performed at a temperature at which a reaction between polymerizable functional groups proceeds, and optimal temperature and time are preferably determined to achieve a desired molecular weight.

When a curable composition is photo-polymerized, among the polymerization conditions, especially UV intensity affects a property of the resulting photochromic cured product. Such an irradiation condition is affected by a type or amount of a photoinitiator or a type of a polymerizable monomer, so it cannot be generally limited, but in general, the conditions are preferably selected so as to give photoirradiation with 50 to 500 mW/cm$^2$ of UV light at a wavelength of 365 nm for 0.5 to 5 minutes.

[Optical Article]

A photochromic compound according to the embodiments can be widely used as a photochromic material, and can be used, for example, as various memory materials alternative to a silver halide photosensitive material, a reprographic material, a photosensitive material for printing, a memory material for a cathode ray tube, a photosensitive material for a laser, a photosensitive material for holography, and various other memory materials. The photochromic material can also be used as a material for a photochromic lens material, an optical filter material, a display material, a light meter, and a decoration material.

The photochromic compound according to the embodiment is particularly suitable for a photochromic lens application. A photochromic lens is suitable as a lens for eyeglasses such as sunglasses. Any known method for producing a photochromic lens can be employed, as long as the method provides uniform photochromic performance.

In the case where a photochromic property is developed by a kneading method, a photochromic cured product in a form of an optical material such as a lens may be obtained by injecting the above-mentioned curable composition between glass molds held with an elastomeric gasket or a spacer and then heating the curable composition in an air furnace or cast-polymerizing the curable composition by irradiation with an active energy ray such as ultraviolet ray depending on a type of a polymerizable compound or a polymerization accelerator.

In the case where a photochromic property is developed by a lamination method, a photochromic layer made of a photochromic cured product is formed on a surface of an optical substrate by dissolving a curable composition in an organic solvent as appropriate to prepare a coating solution; coating a surface of an optical substrate such as a lens substrate with the coating solution by spin coating, dipping, or the like; drying to remove the organic solvent; and then polymerization-curing the curable composition with UV irradiation, heating, or the like in an inert gas such as nitrogen (coating method).

Furthermore, a photochromic layer made of a photochromic cured product can also be formed on a surface of an optical substrate by casting polymerization using an inner mold in which an optical substrate such as a lens substrate is placed face-to-face in a glass mold so that a predetermined void is formed, the curable composition is injected into this void, and the curable composition is polymerization-cured in this state by UV irradiation, heating, or the like (casting polymerization method).

In the case where a photochromic layer is formed on a surface of an optical substrate by the lamination method (coating method and casting polymerization method) as described above, the surface of the optical substrate may be chemically treated with an alkali solution, an acid solution, or the like, or physically treated with corona discharge, plasma discharge, polishing, or the like in advance in order to enhance adhesion between the photochromic layer and the optical substrate. Of course, it is also possible to provide a transparent adhesive resin layer on the surface of the optical substrate.

In addition, when a photochromic property is developed by a binder method, a photochromic sheet is made by sheet-molding using a curable composition, sandwiched between two transparent sheets (optical sheets), and polymerization-cured as described above to obtain a photochromic laminate with a photochromic layer as an adhesive layer.

In this case, coating with a coating solution in which a curable composition is dissolved in an organic solvent can also be employed to produce a photochromic sheet.

The thus-produced photochromic laminate is, for example, mounted in a mold and then a thermoplastic resin (e.g., polycarbonate) for an optical substrate such as a lens is injection-molded thereon to obtain an optical substrate such as a lens with a photochromic property in a predetermined shape.

The photochromic laminate can also be adhered to a surface of an optical substrate with, for example, an adhesive to obtain a photochromic lens.

Note that, when a photochromic laminate is produced as described above, it is preferred to use, as a polymerizable compound, a urethane- or urea-based polymerizable compound, especially a urethane-based polymerizable compound in order to adjust so as to form polyurethane from the viewpoint of high adhesion especially to an optical substrate.

The above-mentioned curable composition can develop a photochromic property with an excellent color developing density at a high temperature.

A photochromic layer or a photochromic cured product formed from a curable composition can be subjected to post-processing such as staining using a dye such as a disperse dye; formation of a hard coat film using a silane coupling agent or a hard coat agent containing as a main component a sol of silicon, zirconium, antimony, aluminum, tin, tungsten, or the like; formation of a thin film by vapor deposition of a metal oxide such as $SiO_2$, $TiO_2$, $ZrO_2$, or the like; antireflection treatment by a thin film coated with an organic polymer; or antistatic treatment depending on its application.

EXAMPLES

Example 1

First Step

Three hundred milliliters of toluene was added to 20.0 g (20.0 mmol) of an iodine compound represented by Formula (22) below, and azeotropic dehydration was performed until a water content in the toluene was 100 ppm or less. After the azeotropic dehydration, the resultant was slowly cooled to −20° C., and 15 mL of n-BuLi (1.6 mol/L hexane solution) was slowly added dropwise while maintaining −15 to −20° C. After consumption of the raw materials, 6.6 g (30.0 mmol) of 1,1,1,7,7,7-hexafluoro-4-heptanone was slowly added dropwise thereto. After the addition, the resultant was stirred at −15 to −20° C. for 1 hour and then slowly warmed to room temperature. After stirring for 1 hour, the resultant was partitioned by adding 300 ml of water thereto. This operation was repeated three times, and a solvent was removed from the resulting organic layer, followed by purification by chromatography on silica gel to obtain a compound represented by Formula (23) below at a yield of 72%.

[Chem. 35]

(22)

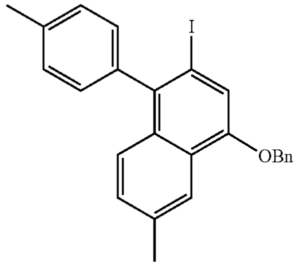

-continued

[Chem. 36]

(23)

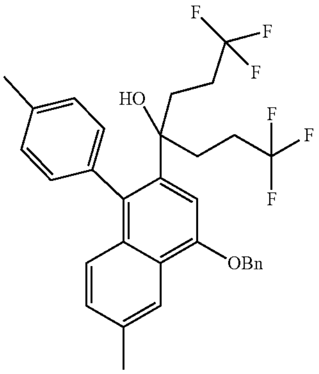

Second Step

After dissolving 8.1 g (14.4 mmol) of the compound of Formula (23) in 165 mL of tetrahydrofuran (THE), 2.0 g of 5% Pd/C (50% water content) was added thereto, and the resultant was reacted under a pressure with hydrogen gas at 0.05 to 0.1 Mpa. After consumption of the raw materials was confirmed, the Pd/C was filtered off, and a solvent was removed from the resulting organic layer to obtain a compound represented by Formula (24) below at a yield of 100%.

[Chem. 37]

(24)

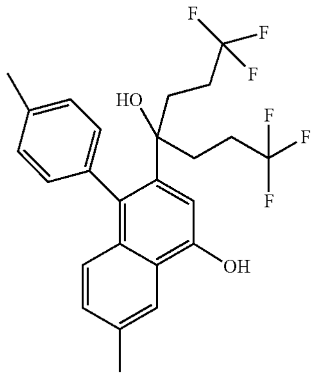

Third Step

First, 350 mL of toluene was added to 14.2 g (75.0 mmol) of p-toluenesulfonic acid monohydrate, and azeotropic dehydration was performed until a water content in the toluene was 300 ppm or less. Then, a toluene solution in which 6.8 g (14.4 mmol) of the Formula (24) was dissolved in 100 mL of toluene was added slowly while maintaining 85 to 100° C., and after the addition, the resultant was refluxed. After consumption of the raw materials was confirmed, the resultant was cooled to room temperature and partitioned by adding 500 mL of water thereto. This operation was repeated three times, and a solvent was removed from the resulting organic layer, followed by purification by chromatography on silica gel to obtain a naphthol derivative represented by Formula (25) below at a yield of 87%.

[Chem. 38]

(25)

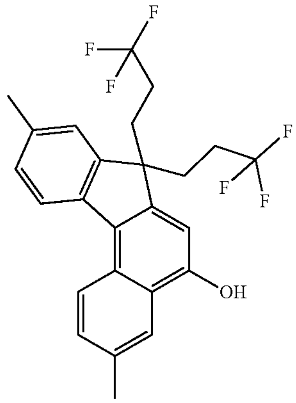

Fourth Step

First, 1.04 g (2.3 mmol) of the naphthol compound of Formula (25) and 0.88 g (3.5 mmol) of propargyl alcohol represented by Formula (26) below were dissolved in 30 mL toluene, and 0.5 g (0.2 mmol) of pyridinium p-toluenesulfonate was added thereto and stirred at 85° C. for 1 hour. After the above reaction, a solvent was removed, followed by purification by chromatography on silica gel to obtain a photochromic compound represented by Formula (27) below at a yield of 79%.

[Chem. 39]

(26)

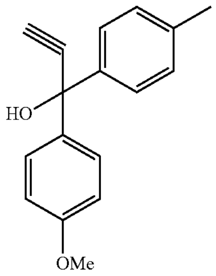

[Chem. 40]

(27)

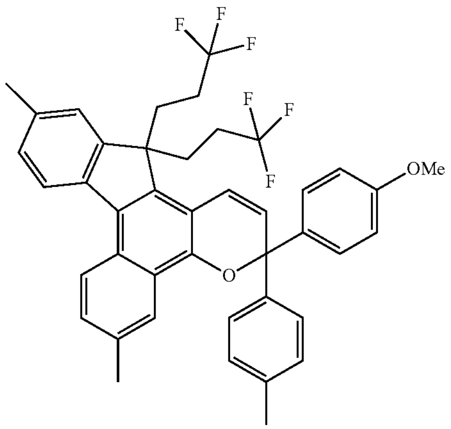

Elemental analysis values for the photochromic compound represented by Formula (27) were determined to be C, 73.42%; H, 5.25%, which are in good agreement with the calculated values for $C_{42}H_{36}F_6O_2$ of C, 73.46%; H, 5.28%.

Proton nuclear magnetic resonance spectra were measured and showed a 17H peak based on a methyl group and a trifluoropropyl group around δ: 0.5 to 3.0 ppm, a 3H peak based on a methoxy group around δ: 3.0 to 5.0 ppm, and a 16H peak based on an aromatic proton and an alkene proton around δ: 5.0 to 9.0 ppm.

Furthermore, $^{13}$C-nuclear magnetic resonance spectra were measured and showed a peak based on a carbon atom in an aromatic ring around δ: 110 to 160 ppm, a peak based on a carbon atom in an alkene around δ: 80 to 140 ppm, and a peak based on a carbon atom in an alkyl between δ: 20 to 60 ppm.

Example 2

First Step

A naphthol derivative represented by Formula (29) below was obtained at a yield of 80% in the same manner as in First to Third steps in Example 1, except that a compound represented by Formula (28) below, which was synthesized with reference to the method described in Patent Document 6, was used instead of the compound of Formula (22).

[Chem. 41]

(28)

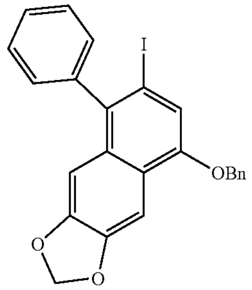

[Chem. 42]

(29)

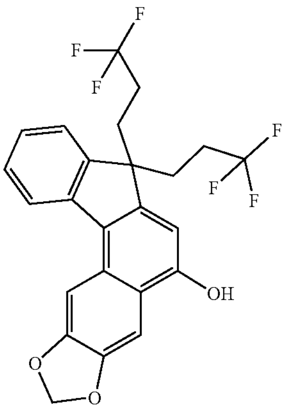

Second Step

A photochromic compound represented by Formula (31) below was obtained at a yield of 76% in the same manner, except that the naphthol derivative of Formula (29) was used instead of the naphthol derivative of Formula (25) and propargyl alcohol represented by Formula (30) below was used instead of the propargyl alcohol of Formula (26) in Fourth step in Example 1.

[Chem. 43]

(30)

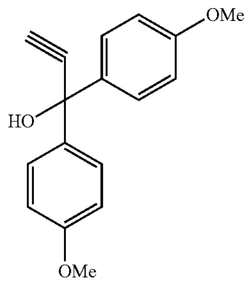

[Chem. 44]

(31)

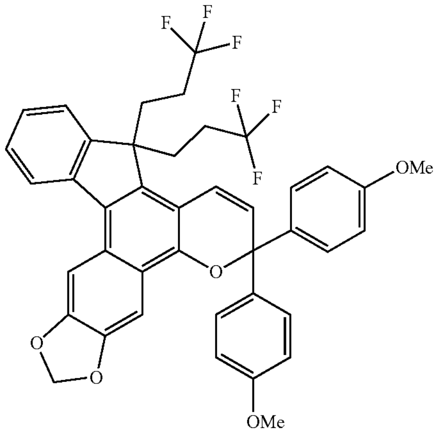

Elemental analysis values for the photochromic compound represented by Formula (31) were determined to be C, 68.49%; H, 4.47%, which are in good agreement with the calculated values for $C_{41}H_{32}F_6O_5$ of C, 68.52%, H: 4.49%.

Proton nuclear magnetic resonance spectra were measured and showed an 8H peak based on a trifluoropropyl group around δ: 0.5 to 3.0 ppm, an 8H peak based on a methoxy group and methylenedioxy around δ: 3.0 to 5.0 ppm, and a 16H peak based on an aromatic proton and an alkene proton around δ: 5.0 to 9.0 ppm.

Furthermore, $^{13}$C-nuclear magnetic resonance spectra were measured and showed a peak based on a carbon atom in an aromatic ring around δ: 110 to 160 ppm, a peak based on a carbon atom in an alkene around δ: 80 to 140 ppm, and a peak based on a carbon atom in an alkyl between δ: 20 to 60 ppm.

Example 3

First Step

A naphthol derivative represented by Formula (33) below was obtained at a yield of 79% in the same manner, except that a compound represented by Formula (32) below was used instead of the compound of Formula (22) and 1,1,1,9,9,9-hexafluoro-5-nonanone was used instead of 1,1,1,7,7,7-hexafluoro-4-heptanone in First to Third steps in Example 1.

[Chem. 45]

(32)

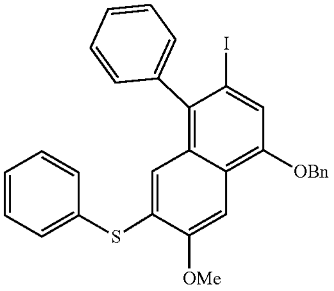

[Chem. 46]

(33)

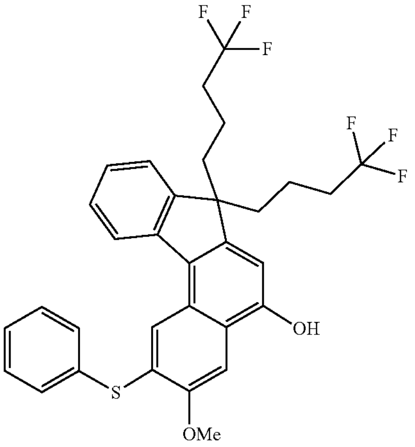

Second Step

A photochromic compound represented by Formula (35) below was obtained at a yield of 76% in the same manner, except that the naphthol derivative of Formula (33) was used instead of the naphthol derivative of Formula (25) and propargyl alcohol represented by Formula (34) below was used instead of the propargyl alcohol of Formula (26) in Fourth step in Example 1.

[Chem. 47]

(34)

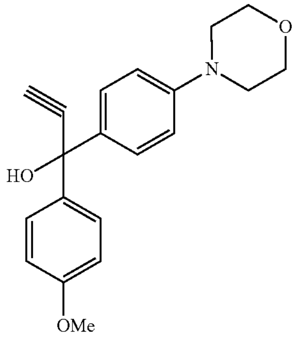

-continued

[Chem. 48]

(35)

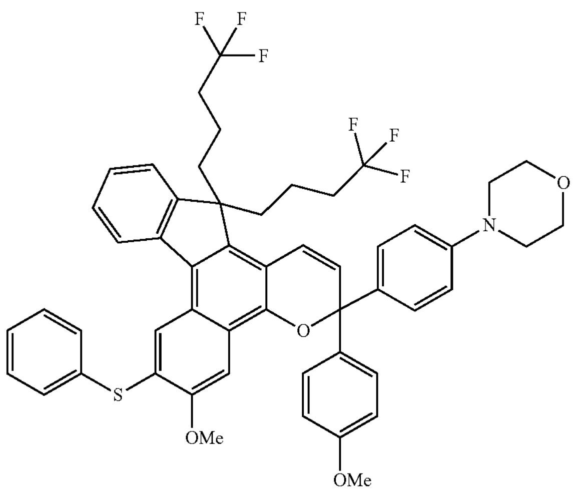

Elemental analysis values for the photochromic compound represented by Formula (35) were determined to be C, 69.68%; H, 5.28%; N, 1.54%; S, 3.59%, which are in good agreement with the calculated values for $C_{52}H_{47}F_6NO_4S$ of C, 69.71%; H, 5.29%; N, 1.56%; S, 3.58%.

Proton nuclear magnetic resonance spectra were measured and showed a 12H peak based on a trifluorobutyl group around δ: 0.5 to 3.0 ppm, a 14H peak based on a methoxy group and a morpholino group around δ: 3.0 to 5.0 ppm, and a 21H peak based on an aromatic proton and an alkene proton around δ: 5.0 to 9.0 ppm.

Furthermore, $^{13}$C-nuclear magnetic resonance spectra were measured and showed a peak based on a carbon atom in an aromatic ring around δ: 110 to 160 ppm, a peak based on a carbon atom in an alkene around δ: 80 to 140 ppm, and a peak based on a carbon atom in an alkyl between δ: 20 to 70 ppm.

Example 4

First Step

First, 26.7 g (62.4 mmol) of a compound represented by Formula (36) below, which was synthesized from 4-methoxy-4'-bromobenzophenone with reference to the method described in Patent Document 7, was dispersed in 100 mL of methanol. Then, 125 mL of an aqueous solution of 12.5 g (312 mmol) of sodium hydroxide was added to this solution and the resultant was refluxed for 3 hours. After the above reaction, the resultant was washed with concentrated hydrochloric acid and then water, a solvent was removed therefrom, and the resultant was purified by reslurrying with 300 mL of toluene to obtain a carboxylic acid compound represented by Formula (37) below at a yield of 90%.

[Chem. 49]

(36)

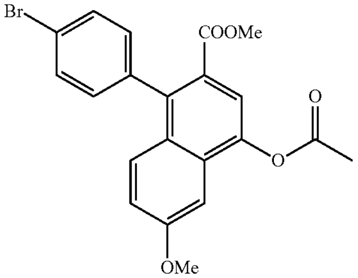

[Chem. 50]

(37)

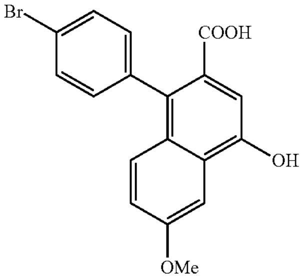

Second Step

First, 20.9 g (56.1 mmol) of the compound represented by Formula (37) and 15.7 g (123.6 mmol) of benzyl chloride were dissolved in 120 mL of DMF. Then, 19.4 g (140.6 mmol) of potassium carbonate was added to this solution, and the resultant was warmed to 80° C. and stirred for 3 hours. After the above reaction, a solvent was removed by washing with water. Then, 200 mL of isopropyl alcohol was added thereto, 220 mL of an aqueous solution of 22.4 g (561.0 mmol) of sodium hydroxide was added thereto, and the resultant was refluxed for 4 hours. After the above reaction, the resultant was cooled to 0 to 5° C. and partitioned by adding concentrated hydrochloric acid thereto to pH 1. A solvent was removed by washing with 500 mL of water twice. The resultant was purified by reslurrying with 300 mL of toluene to obtain a carboxylic acid compound represented by Formula (38) below at a yield of 89%.

[Chem. 51]

(38)

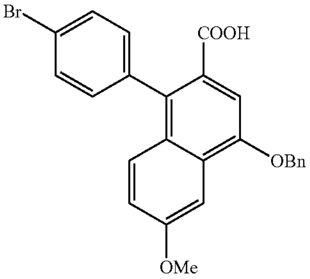

Third Step

First, 10.3 g (54.3 mmol) of p-trifluoromethylphenylboronic acid, 11.5 g (108.7 mmol) of sodium carbonate, 103.5 mL of water, 121.5 mL of 1,2-dimethoxyethane, and 12.2 mL of ethanol were added to 23.1 g (49.9 mmol) of the carboxylic acid compound represented by Formula (38) and the resultant was stirred while bubbling with nitrogen. The nitrogen bubbling was continued for about 20 minutes, and then 142.7 mg (0.1 mmol) of $Pd(PPh_3)_4$ was added thereto and the resultant was reacted at 75° C. for 2 hours. After the above reaction, the resultant was cooled to room temperature, 650 mL of THE was added thereto, and the resultant was cooled to 0 to 5° C. and partitioned by adding concentrated hydrochloric acid thereto to pH 1. A solvent was removed by washing with 500 ml of water twice. The resultant was purified by reslurrying with 300 mL of methanol to obtain a carboxylic acid compound represented by Formula (39) below at a yield of 99%.

[Chem. 52]

(39)

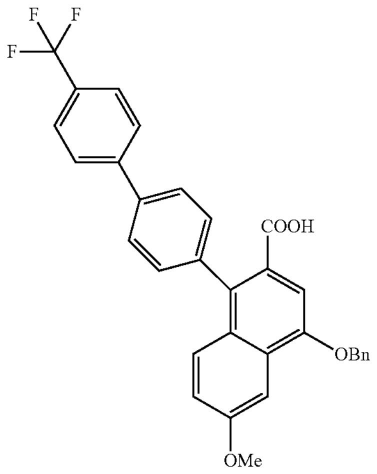

Fourth Step

First, 26.1 g (49.4 mmol) of the carboxylic acid compound represented by Formula (39) was dispersed in 400 mL of toluene. Next, 24.9 g (247.0 mmol) of triethylamine and 17.7 g (64.6 mmol) of diphenylphosphoryl azide were added to this solution and the resultant was stirred at room temperature for 2 hours. Then, 20.0 g (435.3 mmol) of ethanol was added to this solution and the resultant was reacted at 70° C. for 2 hours. Five hundred milliliters of ethanol and then 30.0 g (535.7 mmol) of potassium hydroxide were added to this solution and the resultant was refluxed for 4 hours. After the above reaction, ethanol was distilled off at normal pressure, 300 mL of tetrahydrofuran was added thereto, and a solvent was removed by washing with 150 ml of water three times. Six hundred milliliters of acetonitrile and 150.0 g (247.0 mmol) of 6% hydrochloric acid aqueous solution were added thereto and the resultant was cooled to 0° C. to 5° C. Then, 15.3 g (74.1 mmol) of 33% sodium nitrite aqueous solution was added to this solution and the resultant was stirred for 30 minutes. Next, 41.2 g (247.0 mmol) of 50% potassium iodide aqueous solution was added to this solution and the resultant was stirred at room temperature for 4 hours. After the above reaction, 500 mL of toluene was added thereto and the resultant was washed with 300 ml of water three times. A solvent was removed from the resulting organic layer, followed by purification by chromatography on silica gel to obtain a compound represented by Formula (40) below at a yield of 70%.

[Chem. 53]

(40)

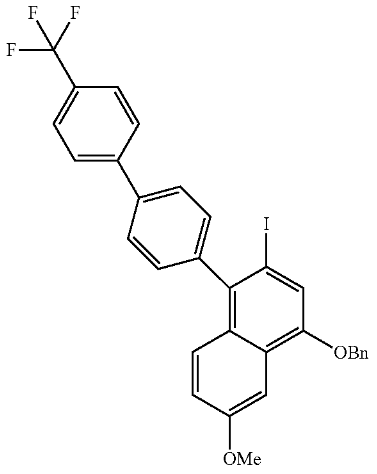

Fifth Step

A naphthol derivative represented by Formula (41) below was obtained at a yield of 76% in the same manner as in First to Third steps in Example 1, except that the compound represented by Formula (40) was used.

[Chem. 54]

(41)

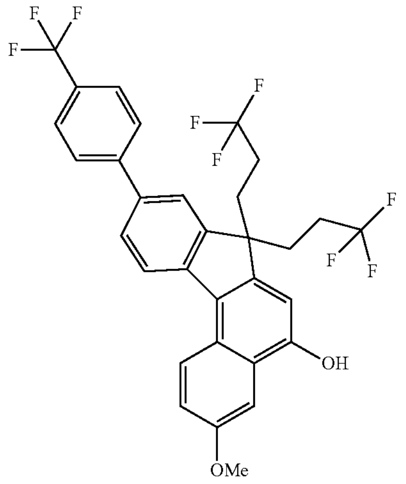

Sixth Step

A photochromic compound represented by Formula (42) below was obtained at a yield of 75% in the same manner, except that the naphthol derivative of Formula (41) was used instead of the naphthol derivative of Formula (33) in Second step in Example 2.

[Chem. 55]

(42)

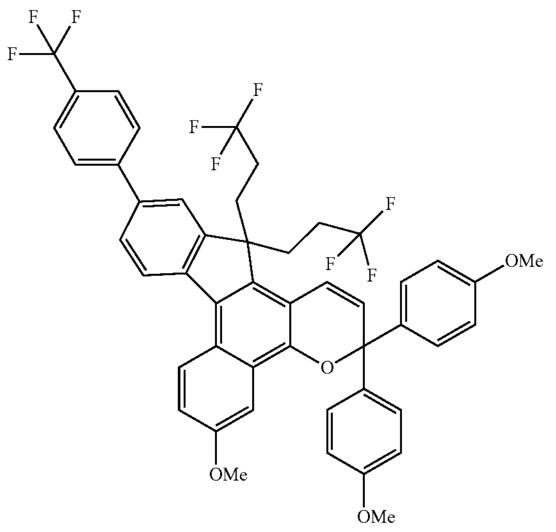

Elemental analysis values for the photochromic compound represented by Formula (42) were determined to be C, 67.87%; H, 4.43%, which are in good agreement with the calculated values for $C_{48}H_{37}F_9O_4$ of C, 67.92%, H: 4.39%.

Proton nuclear magnetic resonance spectra were measured and showed an 8H peak based on a trifluoropropyl group around δ: 0.5 to 3.0 ppm, a 9H peak based on a methoxy group around δ: 3.0 to 5.0 ppm, and a 20H peak based on an aromatic proton and an alkene proton around δ: 5.0 to 9.0 ppm. Furthermore, $^{13}$C-nuclear magnetic resonance spectra were measured and showed a peak based on a carbon atom in an aromatic ring around δ: 110 to 160 ppm, a peak based on a carbon atom in an alkene around δ: 80 to 140 ppm, and a peak based on a carbon atom in an alkyl between δ: 20 to 60 ppm.

Example 5

First Step

First, 20.1 g (43.1 mmol) of an iodine compound represented by Formula (43) below, 1.0 g (4.3 mmol) of palladium acetate, 42.3 g (431.0 mmol) of potassium acetate, 38.8 g (387.9 mmol) of potassium bicarbonate, 74.9 g (431.0 mmol) of dibromomethane, 260 mL of N, N-dimethylformamide (DMF), 86 mL of N, N-dimethylacetamide (DMAc), 4.2 mL of isopropyl alcohol (IPA), and 43 mL of water were added, heated to 80° C., and then reacted. After consumption of the iodine compound was confirmed, the resultant was allowed to cool to room temperature and then partitioned between 100 ml of water and 300 mL of ethyl acetate. A solvent was removed from the resulting organic layer, followed by purification by chromatography on silica gel to obtain a compound represented by Formula (44) below at a yield of 58%.

[Chem. 56]

(43)

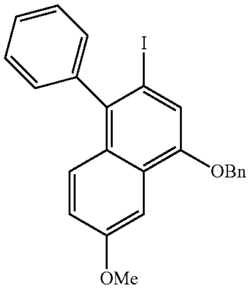

[Chem. 57]

(44)

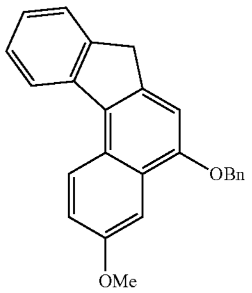

Second Step

First, 1.0 g (2.9 mmol) of the compound represented by Formula (44), 1.0 g (8.6 mmol) of potassium tertiary butoxide (tBuOK), and 50 mL of THE were added and cooled to 0 to 5° C. Then, 1.5 g (8.6 mmol) of 3-bromo-1,1,1-trifluoropropane diluted with 20 mL of THE was added dropwise thereto over 15 minutes. After completion of the addition, the resultant was stirred at room temperature. After consumption of the raw materials was confirmed, the resultant was cooled on ice and partitioned by adding 10 mL of 2% hydrochloric acid and 50 mL of ethyl acetate thereto. Twenty milliliters of water was added to the organic layer for washing with water. This operation was repeated until a pH of an aqueous layer reached 6 to 7. After a solvent was removed from the resulting organic layer, 20 mL of THE and 0.3 g of 5% Pd/C (50% water content) were added thereto, followed by reacting under a pressure with hydrogen gas at 0.05 to 0.1 Mpa. After consumption of the raw materials was confirmed, the Pd/C was filtered off, and a solvent was removed from the resulting organic layer, followed by purification by chromatography on silica gel to obtain a naphthol derivative represented by Formula (45) below at a yield of 74%.

[Chem. 58]

(45)

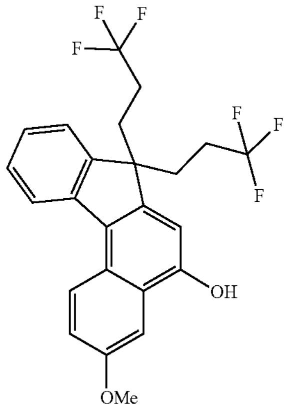

Third Step

A photochromic compound represented by Formula (46) below was obtained at a yield of 72% in the same manner, except that the naphthol derivative of Formula (45) was used instead of the naphthol derivative of Formula (33) in Second step in Example 3.

[Chem. 59]

(46)

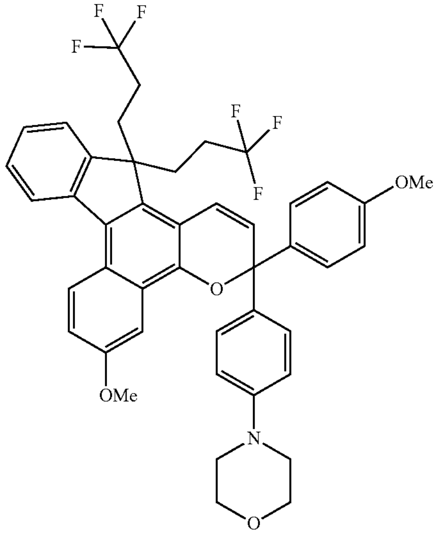

Elemental analysis values for the photochromic compound represented by Formula (46) were determined to be C, 69.52%; H, 5.21%; N, 1.81%, which are in good agreement with the calculated values for $C_{44}H_{39}F_6NO_4$ of C, 69.56%; H, 5.17%; N, 1.84%.

Proton nuclear magnetic resonance spectra were measured and showed an 8H peak based on a trifluoropropyl group around δ: 0.5 to 3.0 ppm, a 14H peak based on a methoxy group and a morpholino group around δ: 3.0 to 5.0 ppm, and a 17H peak based on an aromatic proton and an alkene proton around δ: 5.0 to 9.0 ppm.

Furthermore, $^{13}C$-nuclear magnetic resonance spectra were measured and showed a peak based on a carbon atom in an aromatic ring around δ: 110 to 160 ppm, a peak based on a carbon atom in an alkene around δ: 80 to 140 ppm, and a peak based on a carbon atom in an alkyl between δ: 20 to 70 ppm.

Example 6

First Step

A naphthol derivative represented by Formula (47) below was obtained at a yield of 79% in the same manner, except that 3-bromo-4-methoxybenzophenone was used instead of 3,4-dimethoxy-4'-bromobenzophenone and 4-diphenylaminophenylboronic acid was used instead of 4-trifluorophenylboronic acid in Example 4.

[Chem. 60]

(47)

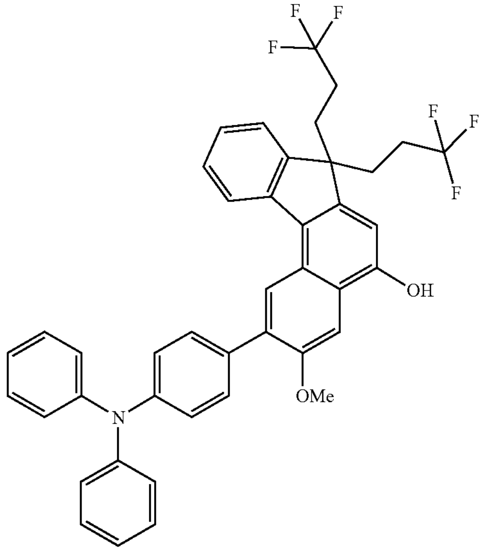

Second Step

A photochromic compound represented by Formula (48) below was obtained at a yield of 77% in the same manner in Example 2, except that the naphthol derivative of Formula (47) was used for the reaction instead of the naphthol derivative of Formula (29).

[Chem. 61]

(48)

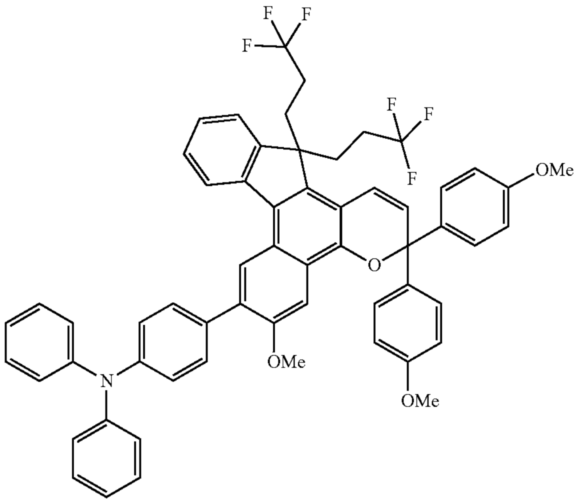

Elemental analysis values for the photochromic compound represented by Formula (48) were determined to be C, 74.70%; H, 5.03%; N, 1.47%, which are in good agreement with the calculated values for $C_{59}H_{47}F_6NO_4$ of C, 74.75%; H, 5.00%; N, 1.48%.

Proton nuclear magnetic resonance spectra were measured and showed an 8H peak based on a trifluoropropyl group around δ: 0.5 to 3.0 ppm, a 9H peak based on a methoxy group around δ: 3.0 to 5.0 ppm, and a 30H peak based on an aromatic proton and an alkene proton around δ: 5.0 to 9.0 ppm.

Furthermore, $^{13}$C-nuclear magnetic resonance spectra were measured and showed a peak based on a carbon atom in an aromatic ring around δ: 110 to 160 ppm, a peak based on a carbon atom in an alkene around δ: 80 to 140 ppm, and a peak based on a carbon atom in an alkyl between δ: 20 to 70 ppm.

Example 7

First Step

A naphthol derivative represented by Formula (50) below was obtained at a yield of 67% in the same manner, except that a compound of Formula (49) below was used instead of the compound of Formula (22) and 1,1,1-trifluoro-4-heptanone was used instead of 1,1,1,7,7,7-hexafluoro-4-heptanone in First step in Example 1.

[Chem. 62]

(49)

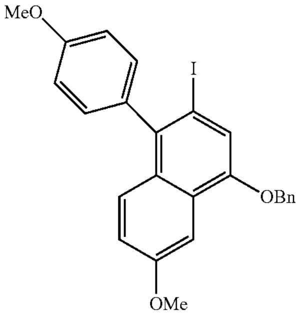

-continued

[Chem. 63]

(50)

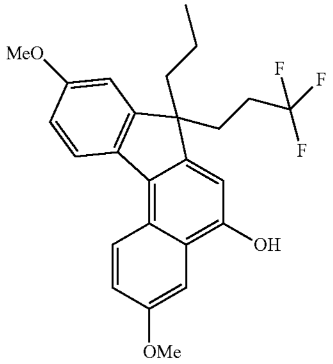

Second Step

A photochromic compound represented by Formula (51) below was obtained at a yield of 70 in the same manner as in Example 2, except that the naphthol derivative of Formula (50) was used instead of the naphthol derivative of Formula (29).

[Chem. 64]

(51)

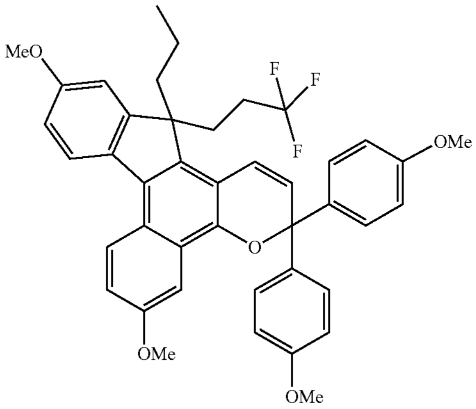

Elemental analysis values for the photochromic compound represented by Formula (51) were determined to be C, 74.08%; H, 5.79%; N, 1.47%, which are in good agreement with the calculated values for $C_{42}H_{39}F_3O_5$ of C, 74.10%, H: 5.77%.

Proton nuclear magnetic resonance spectra were measured and showed an 11H peak based on a trifluoropropyl group and a propyl group around δ: 0.5 to 3.0 ppm, a 12H peak based on a methoxy group around δ: 3.0 to 5.0 ppm, and a 16H peak based on an aromatic proton and an alkene proton around δ: 5.0 to 9.0 ppm.

Furthermore, $^{13}C$-nuclear magnetic resonance spectra were measured and showed a peak based on a carbon atom in an aromatic ring around δ: 110 to 160 ppm, a peak based on a carbon atom in an alkene around δ: 80 to 140 ppm, and a peak based on a carbon atom in an alkyl between δ: 20 to 70 ppm.

Example 8

First Step

A naphthol derivative represented by Formula (52) below was obtained in the same manner, except that 1,1,1,5,5,5-hexafluoro-2-pentanone was used instead of 1,1,1,7,7,7-hexafluoro-4-heptanone in Example 1. Then, this naphthol derivative was reacted with propargyl alcohol in the same manner to obtain a photochromic compound represented by Formula (53) below at a yield of 65%.

[Chem. 65]

(52)

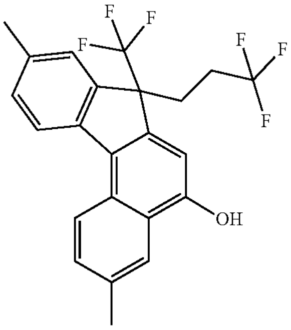

-continued

[Chem. 66]

(53)

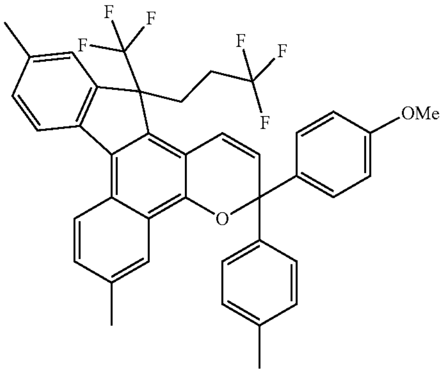

Elemental analysis values for the photochromic compound represented by Formula (53) were determined to be C, 72.90%; H, 4.88%, which are in good agreement with the calculated values for $C_{40}H_{32}F_6O_2$ of C, 72.94%; H, 4.90%.

Proton nuclear magnetic resonance spectra were measured and showed a 13H peak based on a trifluoromethyl group and a methyl group around δ: 0.5 to 3.0 ppm, a 3H peak based on a methoxy group around δ: 3.0 to 5.0 ppm, and a 16H peak based on an aromatic proton and an alkene proton around δ: 5.0 to 9.0 ppm.

Furthermore, $^{13}C$-nuclear magnetic resonance spectra were measured and showed a peak based on a carbon atom in an aromatic ring around δ: 110 to 160 ppm, a peak based on a carbon atom in an alkene around δ: 80 to 140 ppm, and a peak based on a carbon atom in an alkyl between δ: 20 to 70 ppm.

(Analytical Result for Naphthol Derivative)

Table 1 summarizes analytical results of the naphthol derivatives used in Examples 1 to 8.

TABLE 1

| Example | Compound No. | Calculated value C | H | N | S | Determined value C | H | N | S | 1H-NMR |
|---|---|---|---|---|---|---|---|---|---|---|
| 1 | Formula (25) | 66.37 | 4.90 | — | — | 66.35 | 4.89 | — | — | δ0.5-5.0 ppm 14H<br>δ5.0-9.0 ppm 8H |
| 2 | Formula (29) | 61.54 | 3.87 | — | — | 61.51 | 3.90 | — | — | δ0.5-5.0 ppm 10H<br>δ5.0-9.0 ppm 8H |
| 3 | Formula (33) | 65.08 | 4.78 | — | 5.43 | 65.10 | 4.75 | — | 5.44 | δ0.5-5.0 ppm 15H<br>δ5.0-9.0 ppm 13H |
| 4 | Formula (41) | 62.21 | 3.87 | — | — | 62.17 | 3.93 | — | — | δ0.5-5.0 ppm 11H<br>δ5.0-9.0 ppm 12H |
| 5 | Formula (45) | 63.44 | 4.44 | — | — | 63.41 | 4.45 | — | — | δ0.5-5.0 ppm 11H<br>δ5.0-9.0 ppm 9H |
| 6 | Formula (47) | 72.30 | 4.77 | 2.01 | — | 72.28 | 4.79 | 2.04 | — | δ0.5-5.0 ppm 11H<br>δ5.0-9.0 ppm 22H |
| 7 | Formula (50) | 69.76 | 5.85 | — | — | 69.73 | 5.87 | — | — | δ0.5-5.0 ppm 17H<br>δ5.0-9.0 ppm 8H |
| 8 | Formula (52) | 65.09 | 4.28 | — | — | 65.06 | 4.29 | — | — | δ0.5-5.0 ppm 10H<br>δ5.0-9.0 ppm 8H |

(Evaluation of Photochromic Plastic Lens Made by Coating Method for Physical Property)

Example 9

(Preparation of Curable Composition)

First, the photochromic compound obtained in Example 1, a photoinitiator, and a polymerizable compound were mixed to obtain a curable composition.

The polymerizable compound was a combination of the following radical polymerizable monomers:

Polyethylene glycol dimethacrylate (average molecular weight: 736): 42 parts by mass Polyethylene glycol dimethacrylate (average molecular weight: 536): 12 parts by mass Trimethylolpropane methacrylate: 38 parts by mass Y-Methacryloyloxypropyltrimethoxysilane: 2 parts by mass Glycidyl methacrylate: 1 part by mass.

Note that, in the curable composition, the photochromic compound was added in an amount of 0.27 mmol taking a total amount of the radical polymerizable monomers as 100 g.

The following additives were used:

Phenylbis(2,4,6-trimethylbenzoyl) phosphine oxide (photoinitiator: Omnirad 819): 0.3 parts by mass Ethylene bis (oxyethylene) bis[3-(5-tert-butyl-4-hydroxy-m-tolyl) propionate] (stabilizer, Irganox 245): 1 part by mass Bis(1,2,2,6,6-pentamethyl-4-piperidyl)sebacate: 3 parts by mass Leveling agent (L7001) manufactured by DuPont Toray Specialty Materials K.K.: 0.1 parts by mass.

Note that, the above-mentioned additives are described with blended ratios taking a total of the radical polymerizable monomers as 100 parts by mass.

(Production of Optical Article)

Using this curable composition, a photochromic laminate was obtained by a lamination method including polymerization as follows.

First, a thiourethane plastic lens with a center thickness of 2 mm and a refractive index of 1.60 was prepared as an optical substrate. Note that, the thiourethane plastic lens had been alkaline-etched in a 10% sodium hydroxide aqueous solution at 50° C. for 5 minutes in advance, and then thoroughly washed with distilled water.

A spin coater (1H-DX2, manufactured by MIKASA CO., LTD) was used to coat a surface of the above-mentioned plastic lens with a moisture-curing primer (product name: TR-SC-P, manufactured by Tokuyama Corporation) at a rotation speed of 70 rpm for 15 seconds, followed by at 1000 rpm for 10 seconds. Then, about 2 g of the photochromic curable composition obtained as above was spin-coated at a rotation speed of 60 rpm for 40 seconds, followed by at 600 rpm for 10 to 20 seconds so as to achieve a photochromic coating layer with a film thickness of 40 μm.

The lens of which surface had been coated with the photochromic curable composition (photochromic coating layer) was irradiated with light for 90 seconds in a nitrogen gas atmosphere using a metal halide lamp with an output of 200 $mW/cm^2$ to cure the coating. The resultant was then further heated at 110° C. for 1 hour to produce a photochromic laminate with a photochromic layer.

Examples 10 to 16

Photochromic laminates were produced using the photochromic compounds obtained in Examples 2 to 8 (compounds according to Formula (31), Formula (35), Formula (42), Formula (46), Formula (48), Formula (51), and Formula (53)) in the same manner as in Example 9.

Comparative Examples 1 to 3

Photochromic laminates were obtained in the same manner as in Example 9 using photochromic compounds represented by Formulae (A) to (C) below.

[Chem. 67]

(A)

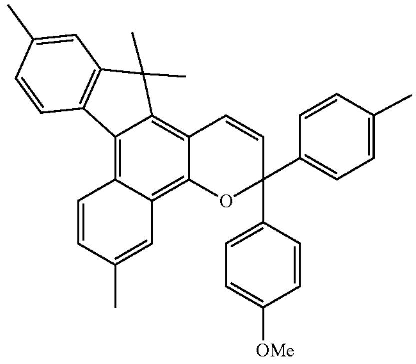

[Chem. 68]

(B)

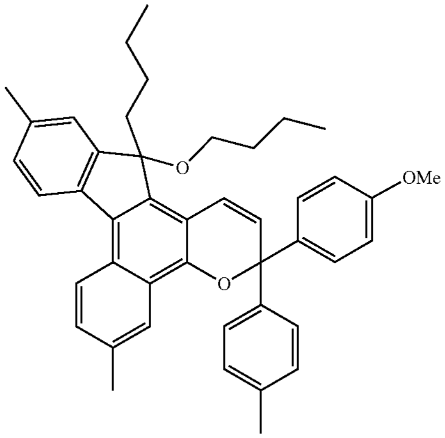

[Chem. 69]

(C)

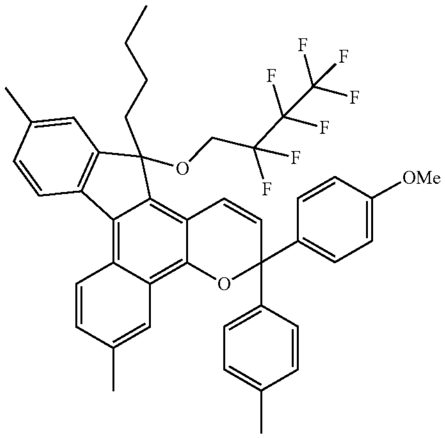

<Evaluation Method>

The resulting photochromic laminates were evaluated by the below-mentioned methods.

(1) Photochromic Property

[1] Maximum Absorption Wavelength (λmax):

This is the maximum absorption wavelength after color development determined by a spectrophotometer manufactured by Otsuka Electronics Co., Ltd. (instantaneous multichannel photo detector MCPD3000) and was used as an index of a color tone upon color development.

[2] Color Developing Density at 23° C. ($A_{23}$):

This is a difference between an absorbance {ε(240)} after irradiation with light at 23° C. for 240 seconds and an absorbance ε(0) when not irradiated with light at the above-mentioned maximum absorption wavelength and was used as an index of a color developing density. The higher this value is, the better photochromic property is.

[3] Color Fading Half-Life at 23° C. [τ½ (Sec).)]:

This is a period of time taken by an absorbance at the above-mentioned maximum absorption wavelength of a sample to decrease to ½ of {ε(240)−ε(0)} when irradiation is stopped after irradiation with light at 23° C. for 240 seconds, and was used as an index of a color fading rate. The shorter this period of time is, the faster the color fading rate is.

[4] Residual ratio ($A_{50}/A_0\times100$): The resulting photochromic plastic lens was subjected to accelerated degradation for 50 hours using a xenon weather meter X25 manufactured by Suga Test Instruments Co., Ltd. Color developing densities were then evaluated as described above before and after a test, and a color developing density before the test ($A_0$) and a color developing density after the test ($A_{50}$) were measured. A ratio ($A_{50}/A_0$) was determined as a residual ratio and was used as an index of color development durability. The higher the residual ratio is, the more durable the color development is.

The results of Examples 9 to 16 are summarized in Table 2. The results of Comparative examples 1 to 3 are summarized in Table 3.

TABLE 2

| | Compound No. | Maximum absorption wavelength (nm) | Color development density at 23° C. (—) | Color fading half-life at 23° C. (sec) | Residual ratio (%) |
|---|---|---|---|---|---|
| Example 9 | Formula | 434 | 0.48 | 46 | 83 |
| | (27) | 551 | 0.89 | 46 | 83 |
| Example 10 | Formula | 454 | 0.57 | 16 | 84 |
| | (31) | 566 | 0.39 | 16 | 84 |
| Example 11 | Formula | 484 | 0.57 | 19 | 82 |
| | (35) | 597 | 0.62 | 19 | 82 |
| Example 12 | Formula | 440 | 0.59 | 21 | 83 |
| | (42) | 576 | 0.77 | 21 | 83 |
| Example 13 | Formula | 458 | 0.35 | 16 | 81 |
| | (46) | 589 | 0.66 | 16 | 81 |
| Example 14 | Formula | 471 | 0.80 | 30 | 87 |
| | (48) | 565 | 0.68 | 30 | 87 |
| Example 15 | Formula | 424 | 0.69 | 78 | 82 |
| | (51) | 592 | 1.05 | 78 | 82 |
| Example 16 | Formula | 432 | 0.55 | 79 | 82 |
| | (53) | 552 | 0.98 | 79 | 82 |

TABLE 3

| | Compound No. | Maximum absorption wavelength (nm) | Color development density at 23° C. (—) | Color fading half-life at 23° C. (sec) | Residual ratio (%) |
|---|---|---|---|---|---|
| Comparative | Formula | 435 | 0.60 | 162 | 79 |
| Example 1 | (A) | 557 | 1.06 | 162 | 79 |
| Comparative | Formula | 438 | 0.53 | 95 | 62 |
| Example 2 | (B) | 561 | 0.99 | 95 | 62 |
| Comparative | Formula | 436 | 0.43 | 47 | 50 |
| Example 3 | (C) | 560 | 0.78 | 47 | 50 |

The only difference between the compounds of Examples 9 and 16 and the compound of Comparative Examples 1 to 3 is a substituent attached to a carbon atom at position 13 of indenonaphthopyran. As can be clearly seen from Tables 2 and 3, the photochromic compounds according to the embodiment are photochromic compounds with superior color fading rate and durability to those of conventional photochromic compounds.

Example 17

First Step

First, 1.70 g (70.0 mmol) of magnesium was placed in a 300 mL 4-necked flask and dried well by heating under reduced pressure, and then 150 mL of dehydrated THE was added thereto and stirred. Then, 1-bromo-4-fluorobutane was slowly added dropwise thereto. After the addition, an internal temperature was slowly heated to reflux until the raw materials were completely consumed to prepare 4-fluorobutylmagnesium bromide.

Second Step

First, 2.95 g (10.0 mmol) of a benzyl-protected compound represented by Formula (54) below, which was synthesized with reference to the method described in Patent Document 6, 2.97 g (70.0 mmol) of lithium chloride, and 17.2 g (70.0 mmol) of anhydrous lanthanum chloride were added to a 500 mL four-necked flask and dried by heating under reduced pressure, and 100 mL of dehydrated THE was added thereto. After stirring, the resultant was cooled to −76° C. A THE solution of 4-fluorobutylmagnesium bromide prepared in First step was added slowly thereto.

[Chem. 70]

(54)

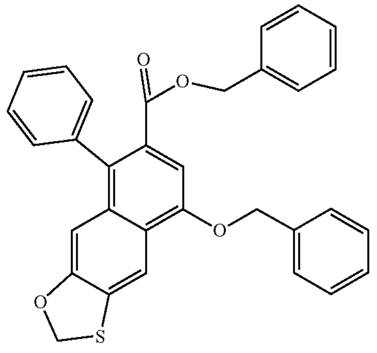

After completion of the addition, an internal temperature was slowly increased to room temperature and the resultant was stirred for 12 hours. After disappearance of the raw materials was confirmed, 300 mL of toluene was added, and 10% hydrochloric acid was added until a pH of an aqueous layer was 1. Then, the resultant was partitioned by adding 300 mL of water thereto and then this operation was repeated until a pH of an aqueous layer was around 7. The resulting organic layer was concentrated and purified by silica gel column chromatography to obtain a compound represented by Formula (55) below at a yield of 85%.

[Chem. 71]

(55)

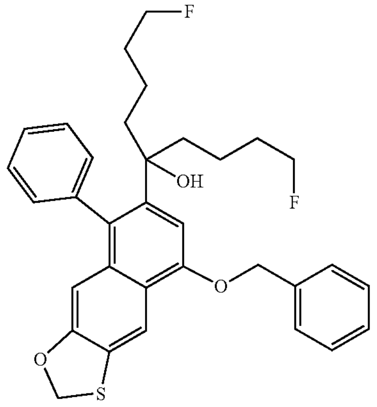

Third Step

A compound represented by Formula (56) below was obtained at a yield of 100% in the same manner, except that the compound of Formula (55) was used for the reaction instead of the compound of Formula (23) in Second step in Example 1.

[Chem. 72]

(56)

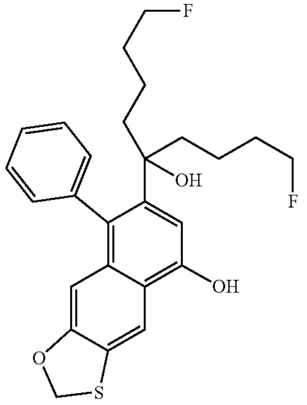

Fourth Step

A naphthol compound represented by Formula (57) below was obtained at a yield of 85% in the same manner, except that the compound of Formula (56) was used instead of the compound of Formula (24) in Third step in Example 1.

[Chem. 73]

(57)

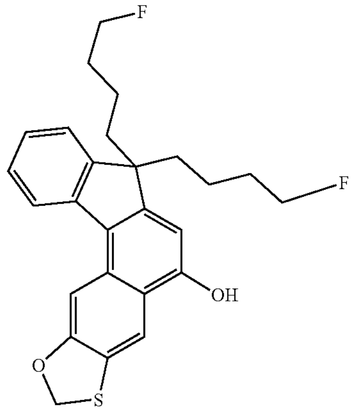

Fifth Step

A photochromic compound represented by Formula (58) below was obtained at a yield of 76% in the same manner, except that the naphthol compound of Formula (57) was used instead of the naphthol compound of Formula (33) in Second step in Example 3.

[Chem. 74]

(58)

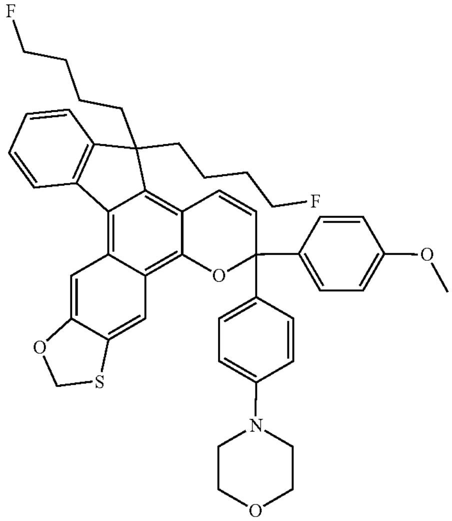

Elemental analysis values for the photochromic compound represented by Formula (58) were determined to be C, 74.04%; H, 6.09%; N, 1.89%; S, 4.33%, which are in good agreement with the calculated values for $C_{46}H_{45}F_2NO_4S$ of C, 74.07%; H, 6.08%; N, 1.88%; S, 4.30%.

Proton nuclear magnetic resonance spectra were measured and showed a 16H peak based on a fluorobutyl group around δ: 0.5 to 3.0 ppm, a 13H peak based on a methoxy group, a morpholino group, and a methylene group around δ: 3.0 to 5.0 ppm, and a 16H peak based on an aromatic proton and an alkene proton around δ: 5.0 to 9.0 ppm.

Furthermore, $^{13}C$-nuclear magnetic resonance spectra were measured and showed a peak based on a carbon atom in an aromatic ring around δ: 110 to 160 ppm, a peak based on a carbon atom in an alkene around δ: 80 to 140 ppm, and a peak based on a carbon atom in an alkyl between δ: 20 to 70 ppm.

Example 18

First Step

A carboxylic acid compound represented by Formula (59) below was synthesized from 4,4'-dimethylbenzophenone with reference to the method described in Patent Document 7.

[Chem. 75]

(59)

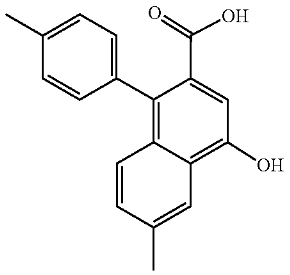

Then, 95.4 g (500.0 mmol) of p-toluenesulfonic acid monohydrate and 1000 mL of toluene were added to 29.2 g (100.0 mmol) of the resulting carboxylic acid, followed by reacting while azeotropic dehydration was performed. After consumption of the raw materials was confirmed, the resultant was cooled to room temperature and the resulting solid was filtered to obtain a carbonyl compound represented by Formula (60) below at a yield of 87%.

[Chem. 76]

(60)

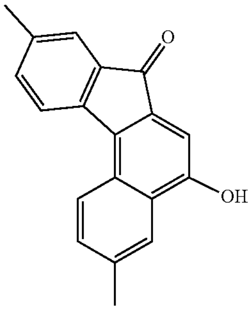

Second Step

The carbonyl compound represented by Formula (60) was reacted to obtain a naphthol derivative represented by Formula (61) below at a yield of 80% with reference to the method described in Patent Document 8.

[Chem. 77]

(61)

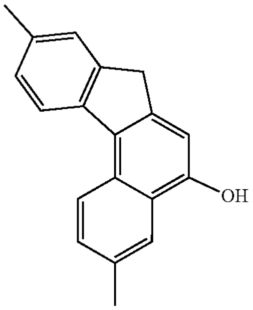

Third Step

A compound represented by Formula (63) below was obtained at a yield of 79% in the same manner, except that the compound of Formula (61) was used instead of the compound of Formula (25) and propargyl alcohol of Formula (62) below was used instead of the propargyl alcohol of Formula (26) in Fourth step in Example 1.

[Chem. 78]

(62)

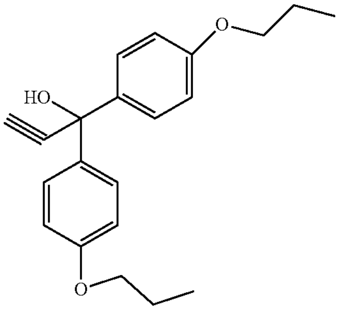

[Chem. 79]

(63)

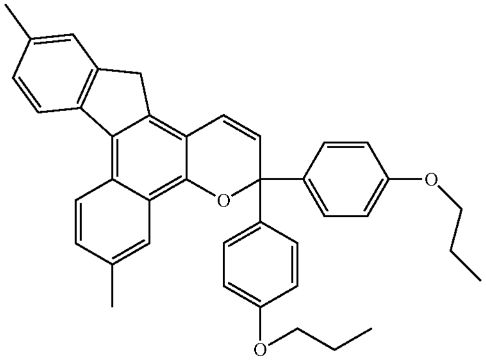

Fourth Step

Thirty milliliters of dehydrated THE was added to 1.7 g (3.0 mmol) of the compound represented by Formula (63) and 2.1 g (15.0 mmol) of 1-bromo-3-fluoropropane and stirred. After dissolving, an internal temperature was cooled to 3° C., and 10 mL of a solution in which 1.0 g (9.0 mmol) of potassium tertiary butoxide is dispersed in THE was slowly added dropwise. After the addition, the resulting reaction liquid was warmed to slowly to room temperature. After disappearance of the raw materials, 10% hydrochloric acid was added until a pH of an aqueous layer was 1, and the resultant was partitioned by adding 30 mL of toluene thereto. The resultant was partitioned by adding 20 ml of water thereto. The resultant was repeatedly partitioned until a pH of the aqueous layer was 6 to 7, and a solvent was removed from the resulting organic layer, followed by purification by chromatography on silica gel to obtain a photochromic compound represented by Formula (64) below at a yield of 81%.

[Chem. 80]

(64)

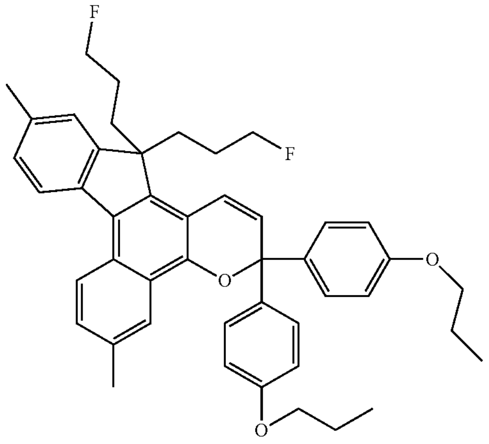

Elemental analysis values for the photochromic compound represented by Formula (64) were determined to be C, 80.41%; H, 7.08%, which are in good agreement with the calculated values for $C_{46}H_{48}F_2O_3$ of C, 80.44%; H, 7.04%.

Proton nuclear magnetic resonance spectra were measured and showed a 28H peak based on a flulropropyl group, a propyloxy group, and a methyl group around δ: 0.5 to 3.0 ppm, a 4H peak based on a propyloxy group around δ: 3.0 to 5.0 ppm, and a 16H peak based on an aromatic proton and an alkene proton around δ: 5.0 to 9.0 ppm.

Furthermore, $^{13}$C-nuclear magnetic resonance spectra were measured and showed a peak based on a carbon atom in an aromatic ring around δ: 110 to 160 ppm, a peak based on a carbon atom in an alkene around δ: 80 to 140 ppm, and a peak based on a carbon atom in an alkyl between δ: 20 to 70 ppm.

Example 19

First Step

A naphthol compound represented by Formula (65) below was synthesized in the same manner, except that 3-bromo-4-methoxymethoxybenzophenone was used for the reaction instead of 4,4'-dimethylbenzophenone in First step in Example 18.

[Chem. 81]

(65)

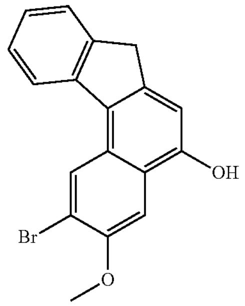

Second Step

A photochromic compound represented by Formula (67) below was obtained at a yield of 86% in the same manner, except that the compound of Formula (65) was used instead of the compound of Formula (25) and propargyl alcohol of Formula (66) below was used instead of the propargyl alcohol of Formula (26) in Fourth step in Example 1.

[Chem. 82]

(66)

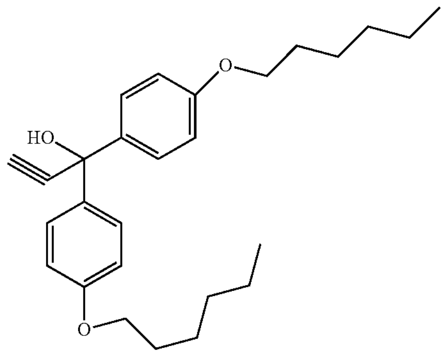

[Chem. 83]

(67)

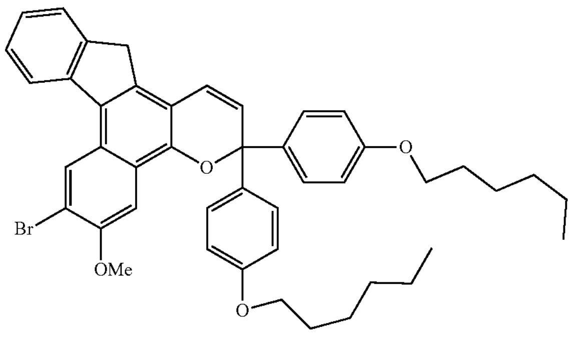

Third Step

A photochromic compound represented by Formula (68) below was obtained at a yield of 87 in the same manner, except that the compound of Formula (67) was used instead of the compound of Formula (63) and 3-bromo-1,1,1-trifluoropropane was used instead of 1-bromo-3-fluoropropane in Fourth step in Example 18.

[Chem. 84]

(68)

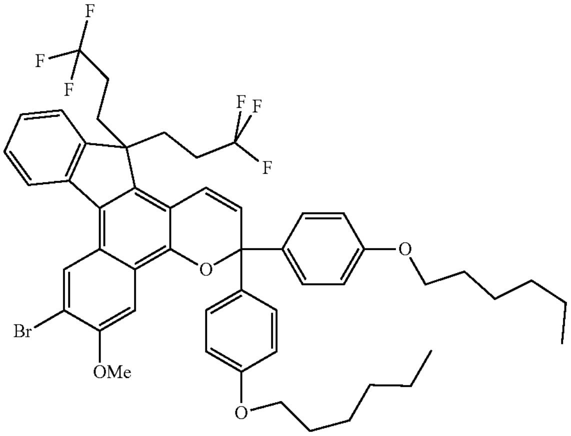

Fourth Step

First, 60 mL of toluene was added to 2.8 g (3.0 mmol) of the compound of Formula (68), 0.4 g (4.2 mmol) of morpholine, and 1.1 g (12.0 mmol) of sodium tertiary butoxide and the resultant was subject to nitrogen bubbling for 20 minutes. Then, 0.05 g (0.06 mmol) of tris(dibenzylideneacetone)dipalladium (0) and 0.1 g (0.24 mmol) of 2-dicyclohexylphosphino-triisopropylbiphenyl was added thereto and the resultant was reacted at 80° C. for 4 hours. After consumption of the raw materials was confirmed, the resultant was cooled at 0 to 5° C. and partitioned by adding 10% hydrochloric acid thereto to pH 6 to 7. The resultant was partitioned by adding 100 mL of water thereto. An aqueous layer was repeatedly washed with water until a pH of the aqueous layer was 6 to 7, and a solvent was removed from the resulting organic layer, followed by purification by chromatography on silica gel to obtain a photochromic compound represented by Formula (69) below at a yield of 72%.

[Chem. 85]

(69)

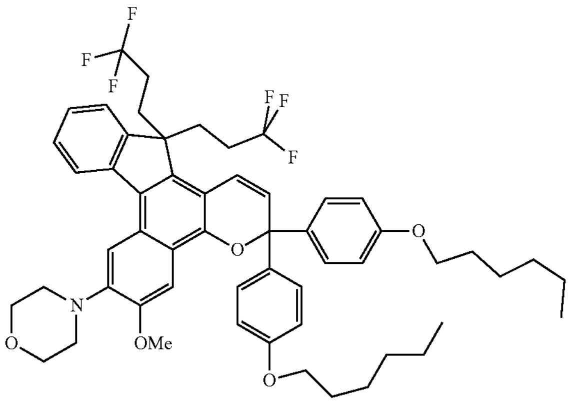

Elemental analysis values for the photochromic compound represented by Formula (69) were determined to be C, 71.07%; H, 6.64%; N, 1.48%, which are in good agreement with the calculated values for $C_5H_{61}F_6NO_5$ of C, 71.03%; H, 6.61%; N, 1.51%.

Proton nuclear magnetic resonance spectra were measured and showed a 34H peak based on a trifluoromethyl group, a hexyloxy group, and a morpholino group around δ: 0.5 to 3.0 ppm, an 11H peak based on a methoxy group, a hexyloxy group, and a morpholino group around δ: 3.0 to 5.0 ppm, and a 16H peak based on an aromatic proton and an alkene proton around δ: 5.0 to 9.0 ppm.

Furthermore, $^{13}$C-nuclear magnetic resonance spectra were measured and showed a peak based on a carbon atom in an aromatic ring around δ: 110 to 160 ppm, a peak based on a carbon atom in an alkene around δ: 80 to 140 ppm, and a peak based on a carbon atom in an alkyl between δ: 20 to 70 ppm.

Example 20

A photochromic compound represented by Formula (70) below was obtained at a yield of 72% in the same manner, except that 2,4-dimethoxyphenylboronic acid was used instead of 4-trifluorphenylboronic acid in Example 4.

[Chem. 86]

(70)

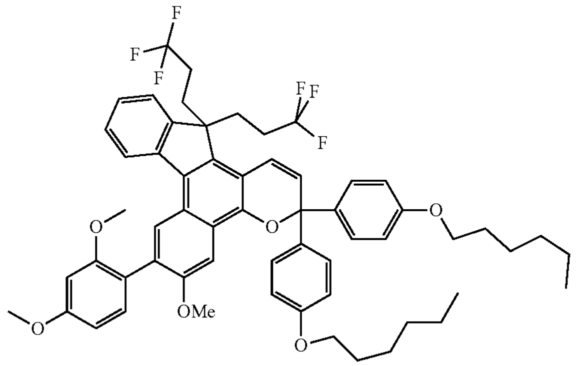

Elemental analysis values for the photochromic compound represented by Formula (70) were determined to be C, 72.26%; H, 6.34%, which are in good agreement with the calculated values for $C_{59}H_{62}F_6O_6$ of C, 72.23%, H: 6.37%.

Proton nuclear magnetic resonance spectra were measured and showed a 30H peak based on a trifluoromethyl group and a hexyloxy group around δ: 0.5 to 3.0 ppm, a 13H peak based on a methoxy group and a hexyloxy group around δ: 3.0 to 5.0 ppm, and a 19H peak based on an aromatic proton and an alkene proton around δ: 5.0 to 9.0 ppm.

Furthermore, $^{13}$C-nuclear magnetic resonance spectra were measured and showed a peak based on a carbon atom in an aromatic ring around δ: 110 to 160 ppm, a peak based on a carbon atom in an alkene around δ: 80 to 140 ppm, and a peak based on a carbon atom in an alkyl between δ: 20 to 70 ppm.

Example 21

First Step

A naphthol compound represented by Formula (71) below was synthesized in the same manner, except that 4-bromo-3',4'-dimethoxymethoxybenzophenone was used for the reaction instead of 4,4'-dimethylbenzophenone in First step in Example 18.

[Chem. 87]

(71)

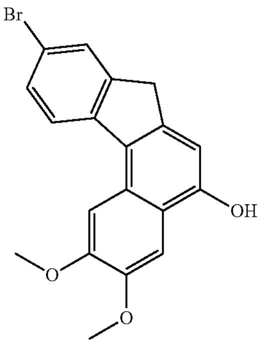

Second Step

A photochromic compound represented by Formula (72) below was synthesized at a yield of 81% in the same manner, except that the naphthol compound of Formula (71) was used instead of the naphthol compound of Formula (29) in Second step in Example 2.

[Chem. 88]

(72)

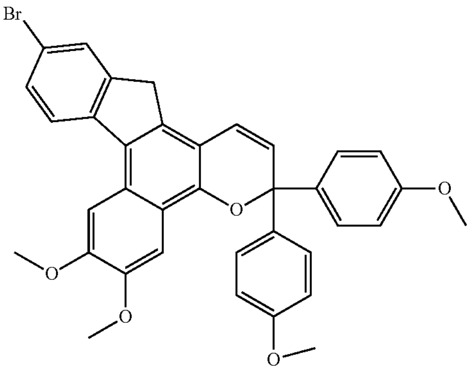

Third Step

A photochromic compound represented by Formula (73) below was synthesized at a yield of 83% in the same manner, except that the compound of Formula (72) was used instead of the compound of Formula (63) and 4-bromo-1,1,1-trifluorobutane was used instead of 1-bromo-3-fluoropropane in Fourth step in Example 18.

[Chem. 89]

(73)

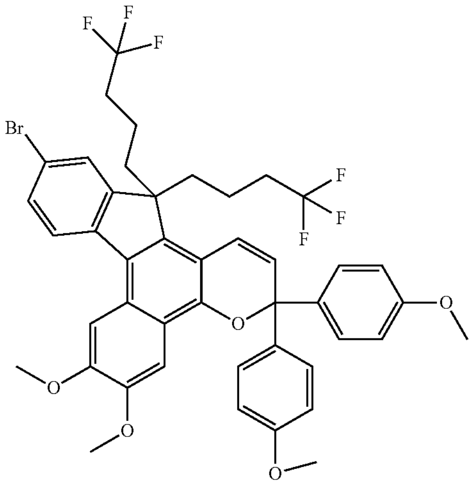

Fourth Step

A photochromic compound represented by Formula (74) below was obtained at a yield of 88% in the same manner, except that 4-methylphenylboronic acid was used for the reaction instead of 4-trifluorphenylboronic acid in Example 4.

[Chem. 90]

(74)

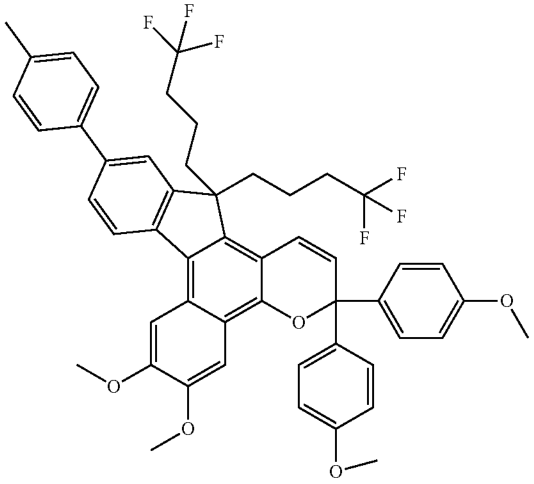

Fifth Step

A photochromic compound represented by Formula (75) below was obtained at a yield of 48% using the compound of Formula (74) with reference to the method described in Patent Document 9.

[Chem. 91]

(75)

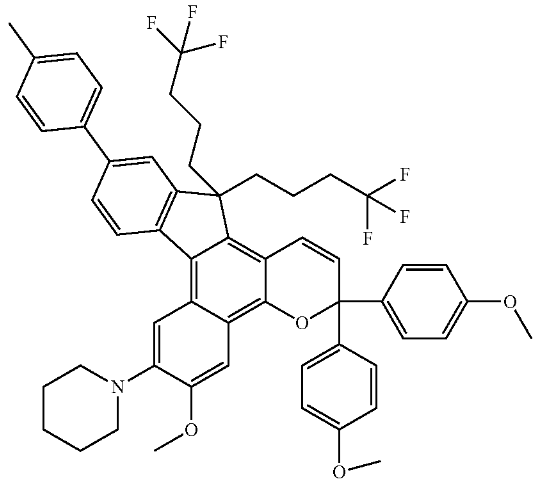

Elemental analysis values for the photochromic compound represented by Formula (75) were determined to be C, 72.88%; H, 5.87%; N, 1.58%, which are in good agreement with the calculated values for $C_{55}H_{53}F_6NO_4$ of C, 72.91%; H, 5.90%; N, 1.55%.

Proton nuclear magnetic resonance spectra were measured and showed a 21H peak based on a trifluoropropyl group, a piperidino group, and a methyl group around δ: 0.5 to 3.0 ppm, a 13H peak based on a methoxy group and a piperidino group around δ: 3.0 to 5.0 ppm, and a 19H peak based on an aromatic proton and an alkene proton around δ: 5.0 to 9.0 ppm.

Furthermore, $^{13}$C-nuclear magnetic resonance spectra were measured and showed a peak based on a carbon atom in an aromatic ring around δ: 110 to 160 ppm, a peak based on a carbon atom in an alkene around δ: 80 to 140 ppm, and a peak based on a carbon atom in an alkyl between δ: 20 to 70 ppm.

Example 22

A photochromic compound represented by Formula (76) below was obtained at a yield of 85% in the same manner, except that 1-bromo-5-fluoropentane was used for the reaction instead of 1-bromo-3-fluoropropane in Fourth step in Example 18.

[Chem. 92]

(76)

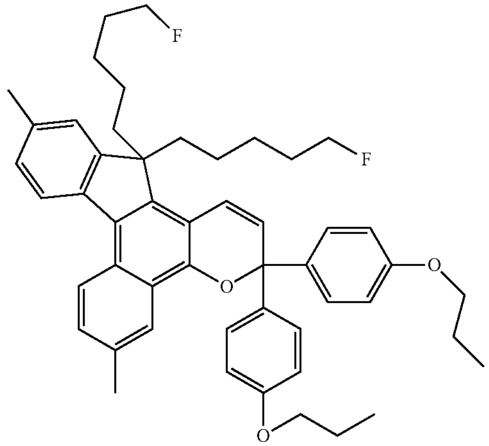

Elemental analysis values for the photochromic compound represented by Formula (76) were determined to be C, 80.80%; H, 7.62%, which are in good agreement with the calculated values for $C_{50}H_{56}F_2O_3$ of C, 80.83%; H, 7.60%.

Proton nuclear magnetic resonance spectra were measured and showed a 36H peak based on a flulropentyl group, a methyl group, and a propoxy group around δ: 0.5 to 3.0 ppm, a 4H peak based on a propoxy group around δ: 3.0 to 5.0 ppm, and a 16H peak based on an aromatic proton and an alkene proton around δ: 5.0 to 9.0 ppm.

Furthermore, $^{13}$C-nuclear magnetic resonance spectra were measured and showed a peak based on a carbon atom in an aromatic ring around δ: 110 to 160 ppm, a peak based on a carbon atom in an alkene around δ: 80 to 140 ppm, and a peak based on a carbon atom in an alkyl between δ: 20 to 70 ppm.

Example 23

A photochromic compound represented by Formula (77) below was obtained at a yield of 81% in the same manner, except that 4-bromo-1,1,1-trifluorobutane was used instead of 1-bromo-3-fluoropropane in Fourth step in Example 18.

[Chem. 93]

(77)

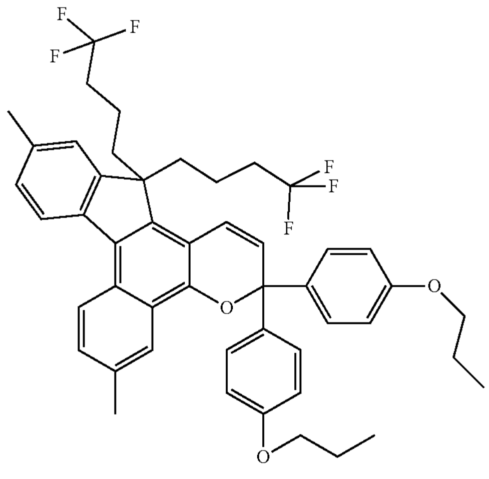

Elemental analysis values for the photochromic compound represented by Formula (77) were determined to be C, 73.24%; H, 6.17%, which are in good agreement with the calculated values for $C_{48}H_{48}F_6O_3$ of C, 73.27%, H: 6.15%.

Proton nuclear magnetic resonance spectra were measured and showed a 28H peak based on a triflulrobutyl group, a methyl group, and a propoxy group around δ: 0.5 to 3.0 ppm, a 4H peak based on a propoxy group around δ: 3.0 to 5.0 ppm, and a 16H peak based on an aromatic proton and an alkene proton around δ: 5.0 to 9.0 ppm.

Furthermore, $^{13}$C-nuclear magnetic resonance spectra were measured and showed a peak based on a carbon atom in an aromatic ring around δ: 110 to 160 ppm, a peak based on a carbon atom in an alkene around: 80 to 140 ppm, and a peak based on a carbon atom in an alkyl between δ: 20 to 70 ppm.

Example 24

A photochromic compound represented by Formula (78) below was obtained at a yield of 82% in the same manner, except that 1-bromo-4-fluorobutane was used instead of 1-bromo-3-fluoropropane in Fourth step in Example 18.

[Chem. 94]

(78)

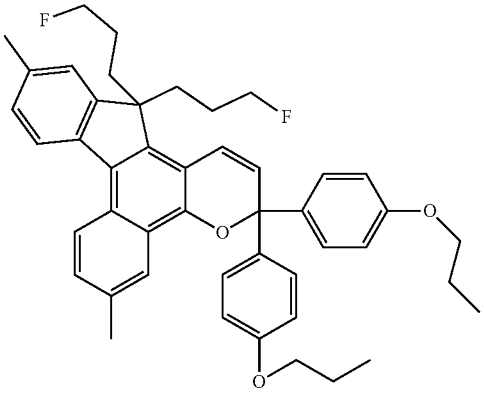

Elemental analysis values for the photochromic compound represented by Formula (78) were determined to be C, 80.40%;

H, 7.02%, which are in good agreement with the calculated values for $C_{46}H_{48}F_2O_3$ of C, 80.44%, H: 7.04%.

Proton nuclear magnetic resonance spectra were measured and showed a 28H peak based on a flulrobutyl group, a methyl group, and a propoxy group around δ: 0.5 to 3.0 ppm, a 4H peak based on a propoxy group around δ: 3.0 to 5.0 ppm, and a 16H peak based on an aromatic proton and an alkene proton around δ: 5.0 to 9.0 ppm.

Furthermore, $^{13}$C-nuclear magnetic resonance spectra were measured and showed a peak based on a carbon atom in an aromatic ring around δ: 110 to 160 ppm, a peak based on a carbon atom in an alkene around δ: 80 to 140 ppm, and a peak based on a carbon atom in an alkyl between δ: 20 to 70 ppm.

Example 25

A photochromic compound represented by Formula (79) below was obtained at a yield of 80% in the same manner, except that 3-bromo-1,1,1-trifluoropropane was used for the reaction instead of 1-bromo-3-fluoropropane in Fourth step in Example 18.

[Chem. 95]

(79)

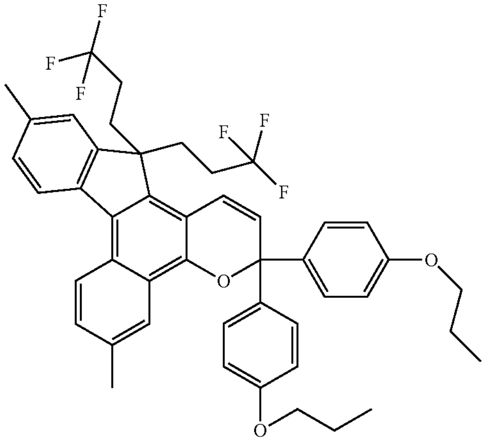

Elemental analysis values for the photochromic compound represented by Formula (79) were determined to be C, 72.78%; H, 5.82%, which are in good agreement with the calculated values for $C_{46}H_4F_6O_3$ of C, 72.81%, H: 5.84%.

Proton nuclear magnetic resonance spectra were measured and showed a 24H peak based on a triflulropropyl group, a methyl group, and a propoxy group around δ: 0.5 to 3.0 ppm, a 4H peak based on a propoxy group around δ: 3.0 to 5.0 ppm, and a 16H peak based on an aromatic proton and an alkene proton around δ: 5.0 to 9.0 ppm.

Furthermore, $^{13}$C-nuclear magnetic resonance spectra were measured and showed a peak based on a carbon atom in an aromatic ring around δ: 110 to 160 ppm, a peak based on a carbon atom in an alkene around δ: 80 to 140 ppm, and a peak based on a carbon atom in an alkyl between δ: 20 to 70 ppm.

Examples 26 to 34

Photochromic laminates were produced using the compounds obtained in Examples 17 to 25 in the same manner as in Example 9. The results of Examples 26 to 34 are summarized in Table 4.

TABLE 4

| | Compound No. | Maximum absorption wavelength (nm) | Color development density at 23° C. (—) | Color fading half-life at 23° C. (sec) | Residual ratio (%) |
|---|---|---|---|---|---|
| Example 26 | Formula | 480 | 0.65 | 37 | 79 |
| | (58) | 592 | 0.62 | 38 | 79 |
| Example 27 | Formula | 434 | 0.47 | 37 | 86 |
| | (64) | 557 | 0.78 | 37 | 86 |
| Example 28 | Formula | 467 | 1.12 | 43 | 80 |
| | (69) | 560 | 0.56 | 43 | 80 |
| Example 29 | Formula | 454 | 0.66 | 32 | 82 |
| | (70) | 568 | 0.60 | 32 | 82 |
| Example 30 | Formula | 477 | 1.75 | 100 | 77 |
| | (75) | 565 | 0.84 | 100 | 79 |

TABLE 4-continued

| | Compound No. | Maximum absorption wavelength (nm) | Color develop-ment density at 23° C. (—) | Color fading half-life at 23° C. (sec) | Residual ratio (%) |
|---|---|---|---|---|---|
| Example 31 | Formula | 434 | 0.64 | 77 | 84 |
| | (76) | 558 | 1.02 | 77 | 83 |
| Example 32 | Formula | 437 | 0.59 | 63 | 86 |
| | (77) | 560 | 0.99 | 63 | 86 |
| Example 33 | Formula | 438 | 0.59 | 70 | 84 |
| | (78) | 561 | 0.97 | 70 | 84 |
| Example 34 | Formula | 438 | 0.42 | 28 | 83 |
| | (79) | 556 | 0.77 | 28 | 84 |

(Use of Resin Composition for Forming Photochromic Layer)

Example 35

(Production of Photochromic Layer (Photochromic Adhesive Layer))

A photochromic layer was prepared as follows.

(Production of Terminal Non-Reactive Urethane Urea Resin for Photochromic Layer Forming Composition)

First, 252 parts by mass of polycarbonate diol with a number average molecular weight of 800, 100 parts by mass of isophorone diisocyanate, and 72 parts by mass of toluene were charged into a 2 L 4-necked flask equipped with a stirring blade, a condense tube, a thermometer, and a nitrogen gas inlet tube and reacted under a nitrogen atmosphere at 100° C. for 7 hours. Thus, a urethane prepolymer with a terminal isocyanate group was synthesized. After the reaction of the above-mentioned urethane prepolymer was completed, the resulting reaction liquid was cooled to about 0° C. and dissolved into 205 parts by mass of isopropyl alcohol and 382 parts by mass of diethyl ketone, and then a temperature of the resulting liquid was kept at 0° C. Next, a mixed solution of 23 parts by mass of bis-(4-aminocyclohexyl) methane serving as a chain extender and 20 parts by mass of diethyl ketone was added dropwise thereto within 30 minutes and reacted at 0° C. for 1 hour. Then, 5.7 parts by mass of 1,2,2,6,6-pentamethyl-4-aminopiperidine was added dropwise thereto and reacted at 0° C. for 1 hour to obtain a solution of a terminal non-reactive urethane urea resin in diethylketone.

One hundred parts by mass of the resulting solution of a terminal non-reactive urethane urea resin, the photochromic compound of Formula (27) (0.27 mmol), 4 parts by mass of an isomer mixture of 4,4'-methylenebis(cyclohexylisocyanate) (polyisocyanate compound), and 0.4 parts by mass of ethylenebis(oxyethylene) bis[3-(5-tert-butyl-4-hydroxy-m-tolyl) propionate] serving as an antioxidant and 0.06 parts by mass of DOW CORNING TORAY L-7001 serving as a surfactant were added and stirred and mixed at room temperature to obtain a photochromic layer forming composition.

(Synthesis of Adhesive for Adhesive Layer and Terminal Non-Reactive Urethane Urea Resin)

A 5 L separable flask (4-necked) equipped with a stirring blade, a condense tube, a thermometer, and a nitrogen gas inlet tube was prepared and 400 parts by mass of polycarbonate diol with a number average molecular weight of 1000, 175 parts by mass of isophorone diisocyanate, and 120 parts by mass of toluene were charged into the flask and reacted under a nitrogen atmosphere at 110° C. for 7 hours. Thus, a urethane prepolymer with a terminal isocyanate group was synthesized. After the reaction of the urethane prepolymer is completed, the resulting reaction liquid is cooled to about 20° C. and dissolved into 2500 parts by mass of propylene glycol monomethyl ether, and then a temperature of the resulting liquid was kept at 20° C. Next, 60 parts by mass of isophoronediamine serving as a chain extender was added dropwise thereto and reacted at 20° C. for 1 hour. Then, 3 parts by mass of n-butylamine was added dropwise thereto and reacted at 20° C. for 1 hour to obtain a solution of a terminal non-reactive urethane urea resin in propylene glycol-monomethyl ether.

Then, 0.2 parts by mass of DOW CORNING TORAY L-7001 serving as a surfactant was added to 500 parts by mass of the resulting solution of a terminal non-reactive urethane urea resin and the resultant was stirred and mixed at room temperature to obtain an adhesive for an adhesive layer.

(Production of Photochromic Layer)

Polycarbonate sheets each having a thickness of 400 μm (first and second optical sheets; one would be an optical substrate and the other would be a layer without a photochromic compound) were coated with the adhesive for an adhesive layer using a coater (manufactured by TESTER SANGYO CO. LTD.) at a coating rate of 0.5 m/min and dried at a drying temperature of 110° C. for 3 minutes to obtain polycarbonate sheets with adhesive resin layers each having a thickness of 5 μm.

Then, an OPP film (oriented polypropylene film) having a thickness of 50 μm using a coater (manufactured by TESTER SANGYO CO. LTD.), was coated with the photochromic layer forming composition at a coating rate of 0.3 m/min and dried at a drying temperature of 100° C. for 5 minutes. Thus, a photochromic layer was formed. Then, the photochromic layer (thickness: 40 μm) was placed onto the adhesive resin layer of the first optical sheet with the adhesive resin layer and laminated together.

Furthermore, a structure formed by releasing the OPP film from the thus-prepared one consisting of the first optical sheet/the adhesive resin layer/the photochromic layer/the OPP film laminated in this order was adhered to the polycarbonate sheet (second optical sheet) with the adhesive resin layer so that the photochromic layer and the adhesive resin layer on the polycarbonate sheet (second optical sheet) were bonded together. The resulting laminate was then left to stand at 40° C. under vacuum for 24 hours, subjected to heat treatment at 110° C. for 60 minutes and humidification treatment at 60° C. and 100% RH for 24 hours, and finally left to stand at 40° C. under vacuum for 24 hours to obtain a photochromic laminate. The resulting photochromic laminate was evaluated in the same manner as for Example 9.

Examples 36 to 38

Photochromic laminates were produced using the photochromic compounds of Formula (46), Formula (48), and Formula (70) in the same manner as in Example 35 and evaluated in the same manner as for Example 9. The results are presented in Table 5.

TABLE 5

| | Compound No. | Maximum absorption wavelength (nm) | Color development density at 23° C. (—) | Color fading half-life at 23° C. (sec) | Residual ratio (%) |
|---|---|---|---|---|---|
| Example 35 | Formula | 436 | 0.49 | 57 | 94 |
| | (27) | 550 | 0.92 | 57 | 94 |
| Example 36 | Formula | 460 | 0.36 | 20 | 93 |
| | (46) | 586 | 0.68 | 20 | 93 |
| Example 37 | Formula | 472 | 0.83 | 40 | 96 |
| | (48) | 563 | 0.70 | 40 | 96 |
| Example 38 | Formula | 457 | 0.67 | 41 | 94 |
| | (70) | 567 | 0.62 | 41 | 95 |

Preferred embodiments of the present invention will be described in addition.

[1]

A photochromic compound having a backbone represented by Formula (1) below:

[Chem. 96]

(1)

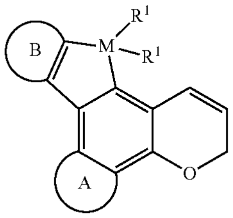

in which

M is C, Si, or Ge;

$R^1$ is a haloalkyl group having 1 or more and 20 or less carbon atoms;

$R^2$ is a substituted or unsubstituted alkyl group having 1 or more and 20 or less carbon atoms or a substituted or unsubstituted haloalkyl group having 1 or more and 20 or less carbon atoms;

Ring A is a substituted or unsubstituted aromatic hydrocarbon ring, a substituted or unsubstituted aromatic heterocyclic ring, or a substituted or unsubstituted fused polycyclic ring in which an aromatic ring or an aromatic heterocyclic ring is fused to any of the above-mentioned rings, or Ring A may not be present; and Ring B is a substituted or unsubstituted aromatic hydrocarbon ring, a substituted or unsubstituted aromatic heterocyclic ring, or a substituted or unsubstituted fused polycyclic ring in which an aromatic ring or an aromatic heterocyclic ring is fused to any of the above-mentioned rings.

[2]

The photochromic compound according to [1], having a backbone represented by Formula (2) below:

[Chem. 97]

(2)

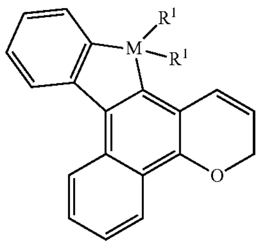

in which $R^1$, $R^2$, and M are each the same as in Formula (1).

[3]

The photochromic compound according to [1] or [2], represented by Formula (3) below:

[Chem. 98]

(3)

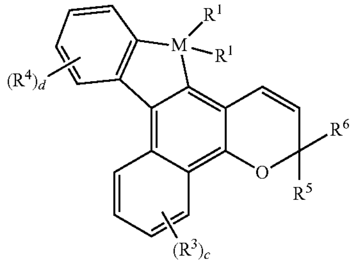

in which $R^1$, $R^2$, and M are each the same as in Formula (1); $R^3$ and $R^4$ are each independently a hydroxyl group, an optionally substituted alkyl group, an optionally substituted haloalkyl group, an optionally substituted cycloalkyl group, an alkoxy group, an amino group, a substituted amino group, an optionally substituted heterocyclic group, a cyano group, a halogen atom, an alkylthio group, an optionally substituted arylthio group, a nitro group, a formyl group, a hydroxycarbonyl group, an alkylcarbonyl group, an alkoxycarbonyl group, an optionally substituted aralkyl group, an optionally substituted aralkoxy group, an optionally substituted aryloxy group, an optionally substituted aryl group, an optionally substituted heteroaryl group, a thiol group, an alkoxyalkylthio group, a haloalkylthio group, or an optionally substituted cycloalkylthio group, an optionally substituted silyl group, an optionally substituted oxysilyl group, a group represented by Formula (X) below, a group represented by $L^1$-$R^{400}$ below, or a group represented by Formula (Y) below;

c is an integer from 0 to 4; when c is 2 to 4, a plurality of $R^3$s may be the same as or different from each other; when c is 2 to 4 and adjacent $R^3$s are present, two adjacent $R^3$s may be taken together with a carbon atom to which $R^3$s are attached to form a ring optionally including an oxygen atom, a carbon atom, a sulfur atom, or a nitrogen atom, and the ring is optionally substituted;

d is an integer from 0 to 4; when d is 2 to 4, a plurality of $R^4$s may be the same as or different from each other; when d is 2 to 4 and adjacent $R^4$s are present, two adjacent $R^4$s may be taken together with a carbon atom to which $R^4$s are attached to form a ring optionally including at least one atom selected from the group consisting of an oxygen atom, a carbon atom, a sulfur atom, and a nitrogen atom and the ring is optionally substituted; and $R^5$ and $R^6$ are each independently an optionally substituted aryl group or an optionally substituted heteroaryl group;

[Chem. 99]

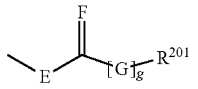

(X)

in formula (X),

E is an oxygen atom or $NR^{101}$ in which $R^{101}$ is a hydrogen atom or an alkyl group;

F is an oxygen atom or a sulfur atom;

G is an oxygen atom, a sulfur atom, or $NR^{202}$ in which $R^{202}$ is a hydrogen atom, an alkyl group, a cycloalkyl group, an aryl group, or a heteroaryl group;

g is 0 or 1;

$R^{201}$ is a hydrogen atom, an alkyl group, a cycloalkyl group, an aryl group, or a heteroaryl group; and when G is an oxygen atom or a sulfur atom, $R^{201}$ is a group other than a hydrogen atom;

in L1-$R^{400}$, $R^{400}$ is a hydrogen atom, an alkyl group, an aryl group, a polymerizable group, a photochromic group, or a silyl group with an alkyl group, an alkoxyl group, or an aryl group as a substituent; and $L^1$ is a group represented by Formula (X2) below;

[Chem. 100]

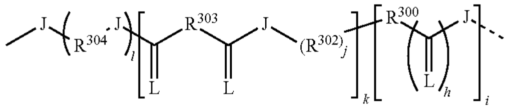

(X2)

in Formula (X2),

J is a divalent group, each independently being directly attached, a substituted methylene group, an oxygen atom, a sulfur atom, or $NR^{301}$ in which $R^{301}$ is a hydrogen atom or an alkyl group;

L is an oxygen atom or a sulfur atom;

$R^{300}$ is an alkylene group, or a silylene group having an alkyl group or an aryl group as a substituent;

$R^{302}$, $R^{303}$, and $R^{304}$ are each independently an alkylene group; h, j, k, and l are an integer of 0 or 1;

i is an integer from 1 to 200, and values of a plurality of units i may be the same as or different from each other; and a dashed line represents an attachment to $R^{400}$;

$$-Q^1-(X^1Q^2)a-X^2Q^3 \qquad (Y)$$

in which $Q^1$ is an alkylene group optionally including a halogen atom as a substituent;

$Q^2$ is an alkylene group optionally including a halogen atom as a substituent;

$Q^3$ is an alkyl group optionally including a halogen atom as a substituent;

$X^1$ and $X^2$ are each independently O, S, $NR^{700}$, $PR^{701}$, or P(=O);

$R^{700}$ is a hydrogen atom, an optionally substituted alkyl group, an optionally substituted cycloalkyl group, an optionally substituted aryl group, or an optionally substituted heteroaryl group;

$R^{701}$ is a hydrogen atom, an optionally substituted alkyl group, an optionally substituted cycloalkyl group, an optionally substituted aryl group, or an optionally substituted heteroaryl group; and a is 0, or 1 or more and 10 or less.

[4]

The photochromic compound according to any one of [1] to [3], in which $R^1$ is a haloalkyl group having 2 or more and 10 or less carbon atoms.

[5]

The photochromic compound according to any one of [1] to [4], in which $R^2$ is a haloalkyl group having 1 or more and 20 or less carbon atoms.

[6]

The photochromic compound according to any one of [1] to [3], in which $R^1$ is a group represented by Formula (1a) below:

$$-(CH_\delta X^{11}{}_\varepsilon)_\theta-CH_\zeta X^{12}{}_\eta \qquad (1a)$$

in Formula (1a), $X^{11}$ and $X^{12}$ are each independently a halogen atom;

$\delta$ and $\varepsilon$ are independently 0 or 1 or 2;

$\delta+\varepsilon=2$;

$\zeta$ is 0 or 1 or 2;

$\eta$ is 1 or more and 3 or less;

$\zeta+\eta=3$; and $\theta$ is 0, or 1 or more and 10 or less.

[7]

The photochromic compound according to [3], represented by Formula (4) below:

[Chem. 101]

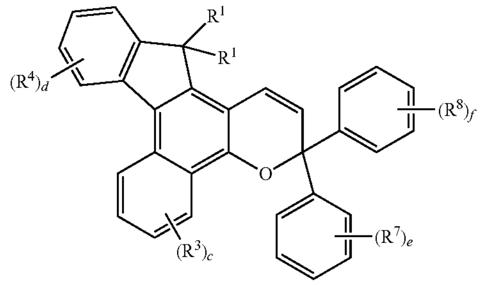

(4)

in which $R^1$, $R^2$, $R^3$, $R^4$, c, and d are each independently the same as in Formula (3);

$R^7$ and $R^8$ are each independently a hydroxyl group, an alkyl group having 1 to 6 carbon atoms, a haloalkyl group having 1 to 6 carbon atoms, a cycloalkyl group having 3 to 8 carbon atoms, an alkoxy group having 1 to 6 carbon atoms, an amino group, a heterocyclic group, a cyano group, a halogen atom, an alkylthio group having 1 to 6 carbon atoms, an optionally substituted arylthio group having 6 to 10 carbon atoms, or the group represented by $L^1$-$R^{400}$;

e is an integer of 0 to 5;

when e is 2 to 5, $R^7$s may be the same as or different from each other;

when adjacent $R^7$s are present, two adjacent $R^7$s may be taken together with a carbon atom to which $R^7$s are attached to form a ring optionally including at least one atom selected from the group consisting of an oxygen atom, a sulfur atom, a carbon atom, and a nitrogen atom and the ring is optionally substituted;

f is an integer of 0 to 5;

when f is 2 to 5, $R^8$s may be the same as or different from each other; and when adjacent $R^8$s are present, two adjacent $R^8$s may be taken together with a carbon atom to which $R^8$s are attached to form a ring optionally including at least one atom selected from the group consisting of an oxygen atom, a sulfur atom, a carbon atom, and a nitrogen atom and the ring is optionally substituted.

[8]

The photochromic compound according to [3] or [6], in which $R^1$ and $R^2$ are the same substituent as each other.

[9]

A curable composition including:

the photochromic compound according to any one of [1] to [8]; and at least one selected from the group consisting of a radical polymerizable monomer, a cationic polymerizable monomer, a compound having a polymerization reactive group, and a (thio)urethane(urea) polymer.

[10]

An optical article including a cured product of the curable composition according to [9].

[11]

A lens including a cured product of the curable composition according to [9].

[12]

Eyeglasses including the lens according to [11].

[13]

A naphthol derivative having a backbone represented by Formula (5) below:

[Chem. 102]

(5)

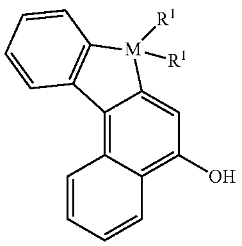

in which

M is C, Si, or Ge;

$R^1$ is a haloalkyl group having 1 or more and 20 or less carbon atoms; and $R^2$ is a substituted or unsubstituted alkyl group having 1 or more and 20 or less carbon atoms or a substituted or unsubstituted haloalkyl group having 1 or more and 20 or less carbon atoms.

The invention claimed is:

1. A photochromic compound having a backbone represented by Formula (1) below:

[Chem. 1]

(1)

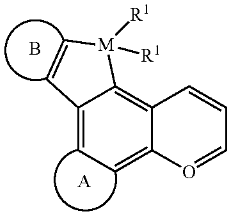

wherein

M is C, Si, or Ge;

$R^1$ is a haloalkyl group having 2 or more and 20 or less carbon atoms;

$R^2$ is a substituted or unsubstituted alkyl group having 2 or more and 20 or less carbon atoms or a substituted or unsubstituted haloalkyl group having 2 or more and 20 or less carbon atoms;

Ring A is a substituted or unsubstituted aromatic hydrocarbon ring, a substituted or unsubstituted aromatic heterocyclic ring, or a substituted or unsubstituted fused polycyclic ring in which an aromatic ring or an aromatic heterocyclic ring is fused to any of the abovementioned rings, or Ring A may not be present; and Ring B is a substituted or unsubstituted aromatic hydrocarbon ring, a substituted or unsubstituted aromatic heterocyclic ring, or a substituted or unsubstituted fused polycyclic ring in which an aromatic ring or an aromatic heterocyclic ring is fused to any of the abovementioned rings.

2. The photochromic compound according to claim 1, having a backbone represented by Formula (2) below:

[Chem. 2]

(2)

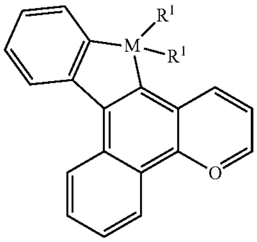

wherein $R^1$, $R^2$, and M are each the same as in Formula (1).

3. The photochromic compound according to claim 1, represented by Formula (3) below:

[Chem. 3]

(3)

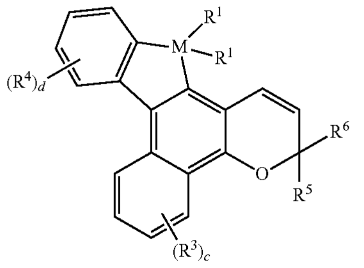

wherein $R^1$, $R^2$, and M are each the same as in Formula (1);

$R^3$ and $R^4$ are each independently a hydroxyl group, an optionally substituted alkyl group, an optionally substituted haloalkyl group, an optionally substituted cycloalkyl group, an alkoxy group, an amino group, a substituted amino group, an optionally substituted heterocyclic group, a cyano group, a halogen atom, an alkylthio group, an optionally substituted arylthio group, a nitro group, a formyl group, a hydroxycarbonyl group, an alkylcarbonyl group, an alkoxycarbonyl group, an optionally substituted aralkyl group, an optionally substituted aralkoxy group, an optionally substituted aryloxy group, an optionally substituted aryl group, an optionally substituted heteroaryl group, a thiol group, an alkoxyalkylthio group, a haloalkylthio group, or an optionally substituted cycloalkylthio group, an optionally substituted silyl group, an optionally substituted oxysilyl group, a group represented by Formula (X) below, or a group represented by Formula (Y) below;

c is an integer from 0 to 4; when c is 2 to 4, a plurality of $R^3$s may be the same as or different from each other;

when c is 2 to 4 and adjacent $R^3$s are present, two adjacent $R^3$s may be taken together with a carbon atom to which $R^3$s are attached to form a ring optionally comprising an oxygen atom, a carbon atom, a sulfur atom, or a nitrogen atom, and the ring is optionally substituted;

d is an integer from 0 to 4; when d is 2 to 4, a plurality of $R^4$s may be the same as or different from each other;

when d is 2 to 4 and adjacent $R^4$s are present, two adjacent $R^4$s may be taken together with a carbon atom to which $R^4$s are attached to form a ring optionally comprising at least one atom selected from the group consisting of an oxygen atom, a carbon atom, a sulfur atom, and a nitrogen atom and the ring is optionally substituted; and $R^5$ and $R^6$ are each independently an optionally substituted aryl group or an optionally substituted heteroaryl group;

[Chem. 4]

(X)

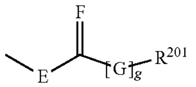

in formula (X),

E is an oxygen atom or $NR^{101}$ in which $R^{101}$ is a hydrogen atom or an alkyl group;

F is an oxygen atom or a sulfur atom;

G is an oxygen atom, a sulfur atom, or $NR^{202}$ in which $R^{202}$ is a hydrogen atom, an alkyl group, a cycloalkyl group, an aryl group, or a heteroaryl group;

g is 0 or 1;

$R^{201}$ is a hydrogen atom, an alkyl group, a cycloalkyl group, an aryl group, or a heteroaryl group; and when G is an oxygen atom or a sulfur atom, $R^{201}$ is a group other than a hydrogen atom;

in $L^1$-$R^{400}$, $R^{400}$ is a hydrogen atom, an alkyl group, an aryl group, a polymerizable group, a photochromic group, or a silyl group with an alkyl group, an alkoxyl group, or an aryl group as a substituent; and $L^1$ is a group represented by Formula (X2) below;

[Chem. 5]

(X2)

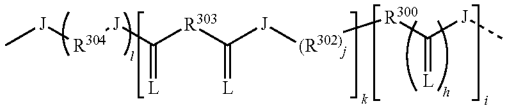

in Formula (X2),

J is a divalent group, each independently being directly attached, a substituted methylene group, an oxygen atom, a sulfur atom, or $NR^{301}$ in which $R^{301}$ is a hydrogen atom or an alkyl group;

L is an oxygen atom or a sulfur atom;

$R^{300}$ is an alkylene group, or a silylene group having an alkyl group or an aryl group as a substituent;

$R^{302}$, $R^{303}$, and $R^{304}$ are each independently an alkylene group;

h, j, k, and l are an integer of 0 or 1;

i is an integer from 1 to 200, and values of a plurality of units i may be the same as or different from each other; and a dashed line represents a bond to $R^{400}$;

$$-Q^1-(X^1Q^2)a-X^2Q^3 \quad (Y)$$

in Formula (Y)

$Q^1$ is an alkylene group optionally comprising a halogen atom as a substituent;

$Q^2$ is an alkylene group optionally comprising a halogen atom as a substituent;

$Q^3$ is an alkyl group optionally comprising a halogen atom as a substituent;

$X^1$ and $X^2$ are each independently O, S, $NR^{700}$, $PR^{701}$, or P(=O);

$R^{700}$ is a hydrogen atom, an optionally substituted alkyl group, an optionally substituted cycloalkyl group, an optionally substituted aryl group, or an optionally substituted heteroaryl group;

$R^{701}$ is a hydrogen atom, an optionally substituted alkyl group, an optionally substituted cycloalkyl group, an optionally substituted aryl group, or an optionally substituted heteroaryl group; and a is 0, or 1 or more and 10 or less.

4. The photochromic compound according to claim 3, represented by Formula (4) below:

[Chem. 6]

(4)

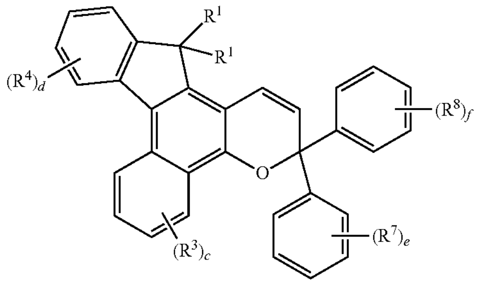

wherein $R^1$, $R^2$, $R^3$, $R^4$, c, and d are each independently the same as in Formula (3);

$R^7$ and $R^8$ are each independently a hydroxyl group, an alkyl group having 1 to 6 carbon atoms, a haloalkyl group having 1 to 6 carbon atoms, a cycloalkyl group having 3 to 8 carbon atoms, an alkoxy group having 1 to 6 carbon atoms, an amino group, a heterocyclic group, a cyano group, a halogen atom, an alkylthio group having 1 to 6 carbon atoms, an optionally substituted arylthio group having 6 to 10 carbon atoms, or the group represented by $L^1$-$R^{400}$;

e is an integer of 0 to 5;

when e is 2 to 5, R's may be the same as or different from each other;

when adjacent $R^7$s are present, two adjacent $R^7$s may be taken together with a carbon atom to which R's are attached to form a ring optionally comprising at least one atom selected from the group consisting of an oxygen atom, a sulfur atom, a carbon atom, and a nitrogen atom and the ring is optionally substituted;

f is an integer of 0 to 5;

when f is 2 to 5, $R^8$s may be the same as or different from each other; and when adjacent $R^8$s are present, two adjacent $R^8$s may be taken together with a carbon atom to which $R^8$s are attached to form a ring optionally comprising at least one atom selected from the group consisting of an oxygen atom, a sulfur atom, a carbon atom, and a nitrogen atom and the ring is optionally substituted.

5. The photochromic compound according to claim 3, wherein $R^1$ and $R^2$ are the same substituent as each other.

6. The photochromic compound according to claim 1, wherein $R^1$ is a haloalkyl group having 2 or more and 10 or less carbon atoms.

7. The photochromic compound according to claim 1, wherein $R^2$ is a haloalkyl group having 2 or more and 10 or less carbon atoms.

8. The photochromic compound according to claim 1, wherein $R^1$ is a group represented by Formula (Ia) below:

$$-(CH_\delta X^{11}{}_\varepsilon)_\theta-CH_\zeta X^{12}{}_\eta \quad (1a)$$

wherein $x^{11}$ and $X^{12}$ are each independently a halogen atom;

δ and ε are independently 0 or 1 or 2;

δ+ε=2;

ζ is 0 or 1 or 2;

η is 1 or more and 3 or less;

ζ+η=3; and

θ is 0, or 1 or more and 10 or less.

9. A curable composition comprising:

the photochromic compound according to claim 1; and at least one selected from the group consisting of a radical polymerizable monomer, a cationic polymerizable monomer, a compound having a polymerization reactive group, and a (thio)urethane(urea) polymer.

10. An optical article comprising a cured product of the curable composition according to claim 9.

11. A lens comprising a cured product of the curable composition according to claim 9.

12. Eyeglasses comprising the lens according to claim 11.

13. A naphthol derivative having a backbone represented by Formula (5) below:

[Chem. 7]

(5)

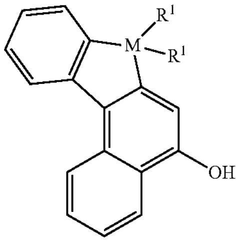

wherein

M is C, Si, or Ge;

$R^1$ is a haloalkyl group having 2 or more and 20 or less carbon atoms; and $R^2$ is a substituted or unsubstituted alkyl group having 2 or more and 20 or less carbon atoms or a substituted or unsubstituted haloalkyl group having 2 or more and 20 or less carbon atoms.

* * * * *